US012262919B2

(12) United States Patent
Lengyel et al.

(10) Patent No.: US 12,262,919 B2
(45) Date of Patent: Apr. 1, 2025

(54) SPINAL ROD-TO-ROD CONNECTORS

(71) Applicant: OrthoPediatrics Corp., Warsaw, IN (US)

(72) Inventors: Rebecca Boerigter Lengyel, Fort Wayne, IN (US); Collin Gibbs, Columbia City, IN (US); Scott Lubensky, Warsaw, IN (US); David Wayne Daniels, Winona Lake, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 250 days.

(21) Appl. No.: 17/798,691

(22) PCT Filed: Jan. 28, 2021

(86) PCT No.: PCT/US2021/015576
§ 371 (c)(1),
(2) Date: Aug. 10, 2022

(87) PCT Pub. No.: WO2021/155061
PCT Pub. Date: Aug. 5, 2021

(65) Prior Publication Data
US 2023/0129404 A1 Apr. 27, 2023

Related U.S. Application Data

(60) Provisional application No. 62/966,761, filed on Jan. 28, 2020.

(51) Int. Cl.
*A61B 17/70* (2006.01)
(52) U.S. Cl.
CPC ...... *A61B 17/7035* (2013.01); *A61B 17/7049* (2013.01); *A61B 17/7032* (2013.01)

(58) Field of Classification Search
CPC ............ A61B 17/7035; A61B 17/7049; A61B 17/705; A61B 17/7052; A61B 17/7032
(Continued)

(56) References Cited

U.S. PATENT DOCUMENTS 6,273,914 B1    8/2001  Papas
8,430,916 B1 *  4/2013  Winslow ............ A61B 17/7007
                                                    606/250

(Continued)

FOREIGN PATENT DOCUMENTS

WO      2021155061 A1   8/2021

OTHER PUBLICATIONS

International Search Report and Written Opinion for International Application No. PCT/US2021/015576, mailed Apr. 26, 2021, 12 pages.

*Primary Examiner* — Eduardo C Robert
*Assistant Examiner* — David C Comstock
(74) *Attorney, Agent, or Firm* — Frost Brown Todd LLP

(57) ABSTRACT

A polyaxial rod connector comprising a body having an external surface. The connector body is intersected by an imaginary first reference plane and an imaginary second reference plane perpendicular to the first plane. The first body portion is on one side of the first plane and defines a first spinal rod passage defining a first passage axis and a first set screw opening defining a first axis perpendicular to the first passage axis. A second body portion is adjoined to the first body portion, defining a second spinal rod passage defining a plurality of passage axes, and a second set screw opening defining a second axis perpendicular to the plurality of second passage axes. The first passage axis is non-parallel with one of second passage axes in the second plane. Either the first or second spinal rod passage have an hourglass shaped cross-section parallel to the second plane.

20 Claims, 17 Drawing Sheets

(58) Field of Classification Search
USPC ........ 606/250, 251, 252, 253, 256, 260, 278
See application file for complete search history.

(56) References Cited

U.S. PATENT DOCUMENTS

| | | | |
|---|---|---|---|
| 11,026,724 B2* | 6/2021 | Ahn .................. | A61B 17/7049 |
| 2006/0116687 A1 | 6/2006 | Miller et al. | |
| 2007/0179501 A1* | 8/2007 | Firkins ................ | A61B 17/705 |
| | | | 606/254 |
| 2011/0106166 A1* | 5/2011 | Keyer .................. | A61B 17/705 |
| | | | 606/279 |
| 2015/0119941 A1 | 4/2015 | Daniels et al. | |
| 2015/0164555 A1 | 6/2015 | Kalfas et al. | |
| 2017/0281237 A1* | 10/2017 | Murray .............. | A61B 17/7004 |
| 2021/0085372 A1* | 3/2021 | Koutsoumbelis .. | A61B 17/7037 |

* cited by examiner

SPINAL ROD-TO-ROD CONNECTORS

BACKGROUND

Spinal fixation systems may be used to surgically fix, adjust, and/or align the spinal column. One type of spinal fixation system employs a spinal fixation rod for supporting the spine and fixing, adjusting, aligning, and/or fusing all or portions of the spinal column into a desired orientation. Attachment of the spinal fixation rod to the spinal column has been achieved using a variety of vertebral anchors (i.e., bone anchors). Vertebral anchors include screws, hooks, pins, and bolts used to engage the vertebrae and connect the spinal rod to vertebrae. Pedicle screws have been used successfully as vertebral anchors. Bone anchors (e.g., pedicle screws) and connectors in combination with spinal rods can align and correct deformities in the natural spinal alignment as well as repair traumatic injury.

At times, a surgeon may wish to connect two spinal fixation rods, for example, in a generally end-to-end configuration. It may be desired to make a connection between two rods to, in effect, make a lengthened rod. However, often the two rods to be connected are not in generally planar, parallel alignment.

Accordingly, there remains an unmet need for an apparatus, system, and method to provide for improved spinal fixation rod connectors.

SUMMARY

A polyaxial rod connector is disclosed. The spinal rod connector can have a connector body having an external surface. The connector body can be intersected by an imaginary first reference plane and an imaginary second reference plane perpendicular to the imaginary first reference plane. The first body portion can be on the first side of the imaginary first reference plane and define openings to a first spinal rod passage defining a first spinal rod passage axis and a first internally threaded set screw opening defining a first set screw axis perpendicular to the first spinal rod passage axis. A second body portion can be adjoined to the first body portion on a second side of the imaginary first reference plane. The second body portion can define openings to a second spinal rod passage defining a plurality of second spinal rod passage axes, and a second internally threaded set screw opening defining a second set screw axis perpendicular to each of the plurality of second spinal rod passage axes. The first spinal rod passage axis can be non-parallel with at least one of the plurality of second spinal rod passage axes in the imaginary second reference plane. One of the first spinal rod passage and the second spinal rod passage can have a generally hourglass shaped cross section parallel to the imaginary second reference plane.

BRIEF DESCRIPTION OF THE DRAWINGS

The present disclosure will be more readily understood from a detailed description of some example embodiments taken in conjunction with the following figures.

DETAILED DESCRIPTION

Figure 1:
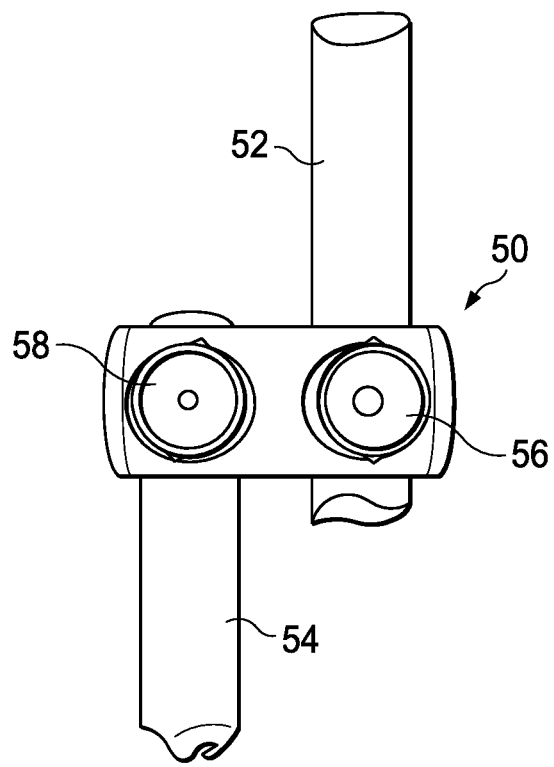
FIG. 1 is a top plan view of a representative spinal fixation rod connector.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Described herein are example embodiments of spinal fixation rod connectors useful for connecting spinal fixation rods in orthopedic procedures that include spinal fixation. In general, the polyaxial connectors described in the examples herein include structure and features that permit a spinal fixation rod to be secured in an opening of the connector in a range of orientations. That is, a spinal fixation rod can be secured in the polyaxial connectors described herein such that at least one of the rods, and, for descriptive purposes, its respective central axis, can be oriented in a range of directions in a plane, the range of directions defining an arc of, in an embodiment, up to and including 40 degrees or more. Thus, polyaxial connectors can connect the ends of connected spinal fixation rods in one or both of a non-planar and a non-parallel relationship.

Referring to FIG. 1, a representative rod-to-rod spinal fixation rod connector 50 is shown. As shown, a first spinal fixation rod 52 and a second spinal fixation rod 54 can be joined by being inserted into respective openings in the spinal fixation rod connector 50 and secured by a first set screw 56 and a second set screw 58, respectively. Each opening in the spinal fixation rod connector is a cylindrical opening into which the spinal fixation rod can be inserted for securement.

Figure 2:
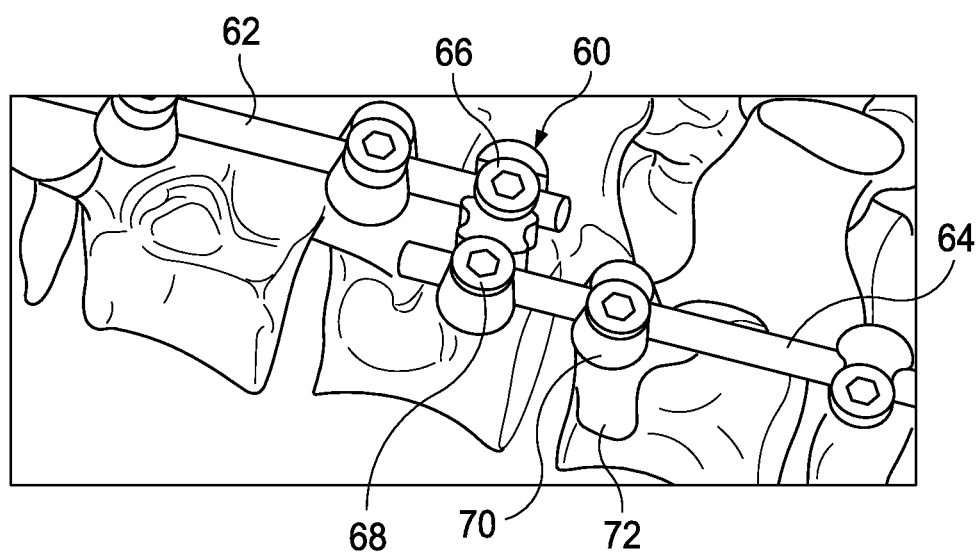
FIG. 2 is a perspective view of a representative spinal fixation rod connector.

Referring to FIG. 2, there is shown another representative rod-to-rod spinal fixation rod connector 60 in use with pedicle screws 70 that are screwed into pedicle bones 72 in a spinal fixation configurations. As shown, a first spinal fixation rod 62 and a second spinal fixation rod 64 can be joined by being inserted into respective openings the rod-to-rod spinal fixation rod connector 60 and secured by a first set screw 66 and a second set screw 68, respectively. Each opening in the spinal fixation rod connector is a cylindrical opening into which the spinal fixation rod can be inserted for securement.

The representative rod-to-rod spinal fixation rod connectors shown in FIGS. 1 and 2 connect the ends of the connected rods in a generally planar (e.g., in the plane of the paper for FIG. 1) and parallel relationship. Often, a surgeon may wish to connect rod ends that are not in a planar or parallel relationship.

Figure 3:
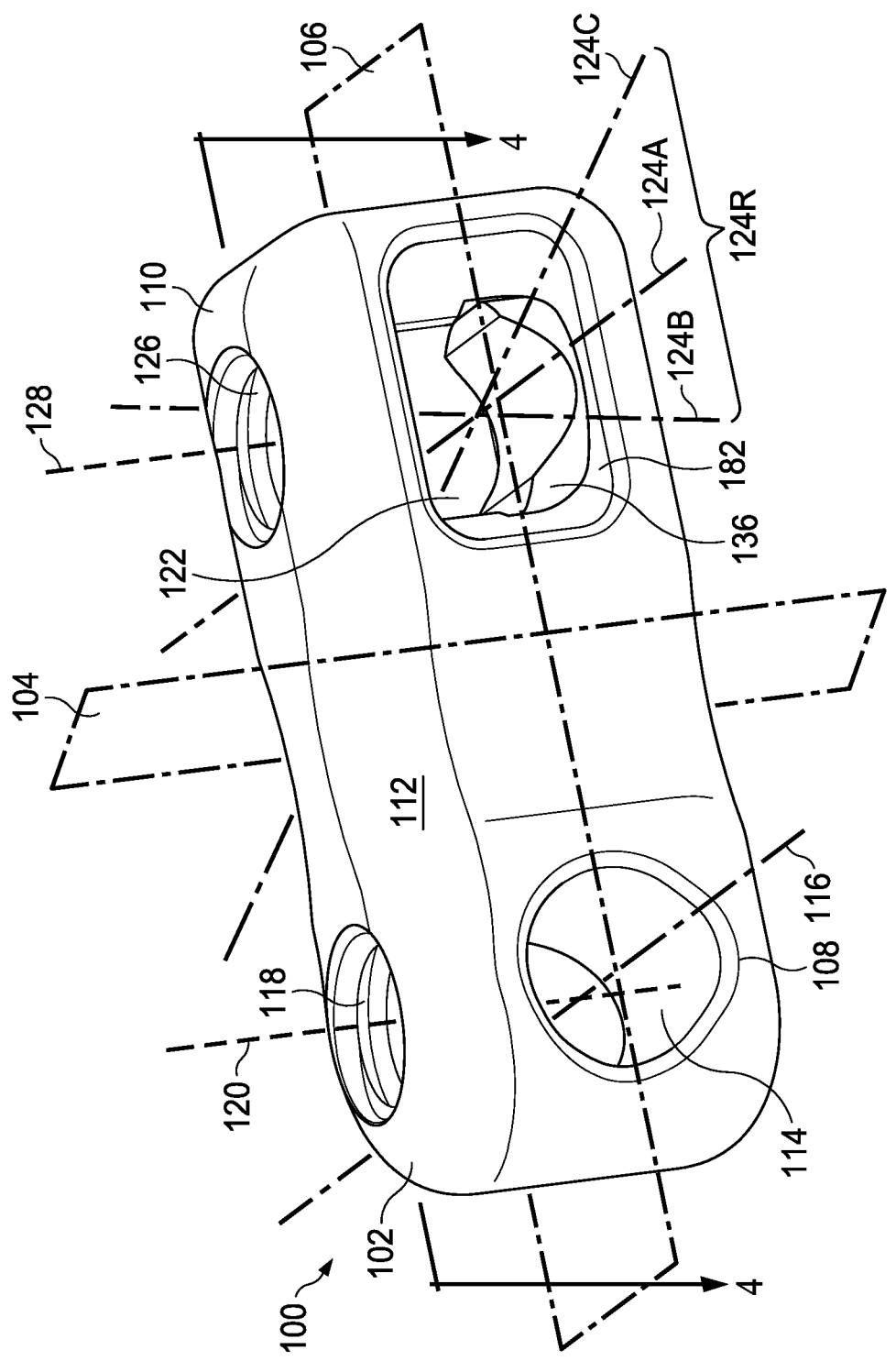
FIG. 3 is a perspective view of a representative spinal fixation rod connector according to one embodiment of the disclosure.

Referring now to FIG. 3, there is shown an example embodiment of a polyaxial connector 100 having a connector body 102. Features and benefits of the polyaxial connector 100 can be understood with reference to two imaginary intersecting, orthogonal planes: an imaginary first reference plane 104 and an imaginary second reference plane 106. The imaginary first reference plane 104 divides the polyaxial connector body into two portions, a first body portion 108 and a second body portion 110. The first body portion 108 can be adjoined to the second body portion 110. By "adjoined" is meant the first body portion 108 and the second body portion 110 lie next to, or are in contact, with one another. In example embodiments the connector body 102 can be unitary, such that the first body portion 108 and the second body portion 110 are simply two sides of a unitary, single-piece body member. In other embodiments, the first body portion 108 and the second body portion 110 can each be discrete parts that can be joined to form a connector body 102.

The imaginary first reference plane 104 can be considered a vertical plane for a polyaxial connector 100 as depicted in FIG. 1. Likewise, the imaginary second reference plane 106 can considered a horizontal plane for a polyaxial connector 100 as depicted in FIG. 3. In general, the terms "vertical," "horizontal," "above," "below," and the like are used herein with respect to the orientation of features as depicted in the FIGS. Each of the imaginary first reference plane 104 and the imaginary second reference plane 106 can bisect the connector into two parts, which parts can be, in an example, equal halves. However, the terms "intersecting," "bisect," "bisecting," "divides" and the like are intended to mean that the imaginary planes described herein for the purposes of describing the structure of the polyaxial connector 100 can divide the polyaxial connector 100 into portions which may not have equal size and shape, but which can also be two portions that are equal, i.e., two halves, as depicted in FIG. 3.

The polyaxial connector 100 has an external surface 112, the external surface defining a plurality of openings that pass through at least a portion of the polyaxial connector 100. The external surface 112 on the first body portion 108 defines openings to a first spinal rod passage 114 defining a first spinal rod passage axis 116. The first spinal rod passage 114 passes completely through the connector body 102 and serves as a passage for connecting a first spinal rod (not shown in FIG. 3, but as shown in FIGS. 1 and 2), the first spinal rod having a first spinal rod axis that can be, when connected, co-axial with the first spinal rod passage axis 116. The external surface 112 on the first body portion 108 defines a first internally threaded set screw opening 118 defining a first set screw axis 120. A first set screw (not shown in FIG. 3, but as shown in FIGS. 1 and 2) can be screwed into the first internally threaded set screw opening 118 to engage and tighten on the first spinal rod inside the first spinal rod passage 114. Once inserted and secured, it can be understood that the end of the first spinal rod can be secured in a fixed position with reference to the imaginary first reference plane 104 and the imaginary second reference plane 106. In an embodiment, once inserted and secured, it the end of the first spinal rod can be secured in a fixed position parallel to one or both of the imaginary first reference plane 104 and the imaginary second reference plane 106. In an embodiment, the first spinal rod passage axis 116 and the first set screw axis 120 are co-planar.

Referring again to FIG. 3, and FIGS. 4 and 5 which are each cross-sectional views of the polyaxial connector 100 shown in FIG. 3, the external surface 112 on the second body portion 110 defines openings to a second spinal rod passage 122 defining a second spinal rod passage axis 124. The second spinal rod passage 122 passes completely through the connector body 102 and serves as a passage for connecting a second spinal rod (not shown in FIG. 3, but as shown in FIGS. 1 and 2), the second spinal rod having a second spinal rod axis that can be, when connected, co-axial with the second spinal rod passage axis 124. The external surface 112 on the second body portion 110 defines a second internally threaded set screw opening 126 defining a second set screw axis 128. The second spinal rod passage 122 has a first passage surface 182 opposite the second internally threaded set screw opening 126, against which is pressed the forces introduced by screwing down the set screw. The second spinal rod can be inserted in the second spinal rod passage 122. A second set screw (not shown in FIG. 3, but as shown in FIGS. 1 and 2) can be screwed into the second internally threaded set screw opening 126 to engage and tighten on the second spinal rod inside the second spinal rod passage 122. Once inserted and secured by the set screw, it can be understood that the end of the second spinal rod can be secured in a fixed position with reference to the imaginary first reference plane 104 and the imaginary second reference plane 106. In an embodiment, once inserted and secured, the end of the second spinal rod can be secured in a fixed position parallel to one or both of the imaginary first reference plane 104 and the imaginary second reference plane 106. In an embodiment, the second spinal rod passage axis 124 and the second set screw axis 128 are co-planar.

Figure 4:
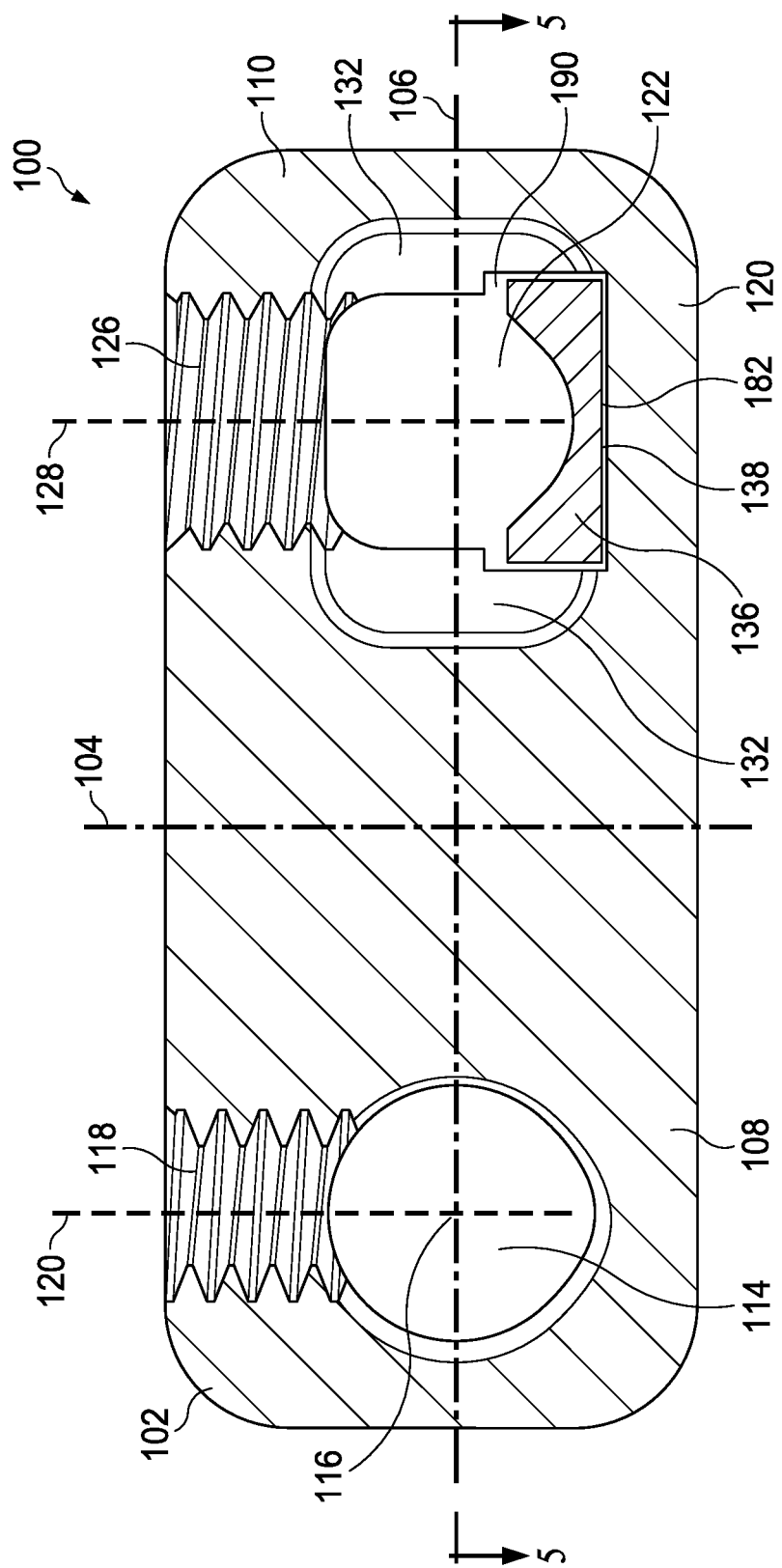
FIG. 4 is a cross-sectional view of the cross-section 4-4 of FIG. 3.
Figure 5:
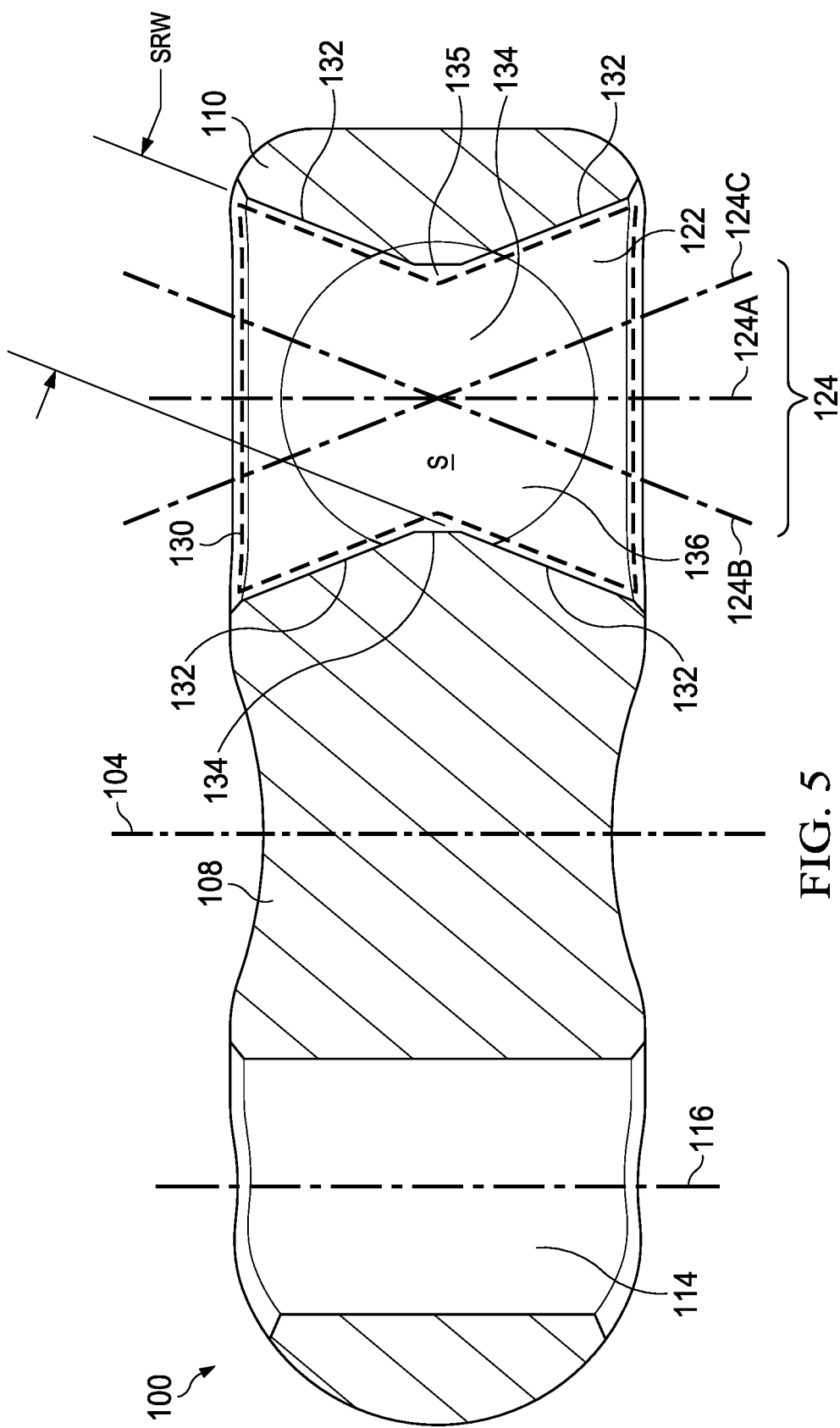
FIG. 5 is a cross-sectional view of the cross-section 5-5 of FIG. 4.

As can be understood with reference to the description herein, including with reference to FIGS. 3-5, one of the first spinal rod passage 114 and the second spinal rod passage 122 can have a size and shape to facilitate variable spinal rod axis positions. For example, as shown in FIGS. 3-5, in an embodiment of the polyaxial connector 100, the first spinal rod passage 114 can be generally cylindrical in shape, while the second spinal rod passage 122 can have a shape S that in cross section at imaginary second reference plane 206 generally approximates an hourglass shape 130, as depicted in a dashed outline in FIG. 5. The term "hourglass shape" is used to describe a cross sectional shape that is defined by the internal sidewalls 132 of the second spinal rod passage that converge internally from the opening on each side of the polyaxial connector 100 external surface 112 toward one another to a vertex 135 on each side at the narrowest throat portion 134 through which a spinal fixation rod can pass to be connected by the polyaxial connector 100. In an embodiment, as discussed below, both of the first and second spinal rod passages can have a shape S that in cross section at imaginary second reference plane 206 generally approximates an hourglass shape 130. The shape S can be any shape that permits variable spinal rod axis positions. Thus, the shape S can be generally rectangular, with dimensions permitting variable spinal rod axis positions. However, it is believed that greater securing accuracy can be achieved when the shape S is defined by internal sidewalls 132 that together approximate an hourglass shape because the internal sidewalls 132 converge to a vertex 135 at a narrowest throat portion 134, with the parallel opposing sidewalls 132 being spaced to a dimension SRW that is at least equal to the width of a spinal rod. The width dimension SRW can range from about 4.0 mm to about 9.0 mm. Likewise, the diameter of any cylindrical shaped spinal rod passages, such as the first spinal rod passage 114 in FIGS. 3-5, can have a diameter of between about 4.0 mm to about 9.0 mm.

The various orientations of second spinal rod passage axes 124 shown, i.e., 124A-124C are simply three examples of what is virtually an infinite range of orientation, that can sweep an arc of, in an embodiment, up to and including 40 degrees, and as disclosed in more detail with reference to FIG. 8, below. In the embodiment depicted in FIGS. 3-5, for example, once inserted in the second spinal rod passage 122, the connected portion of the second spinal rod can be secured at the first variable rod axis 124A such that its axis is generally parallel to the imaginary second reference plane 106 but at an angle to the imaginary first reference plane 104. In this manner a non-parallel alignment of a first spinal rod end and a second spinal rod end can be accommodated and joined in a plane.

Figure 11:
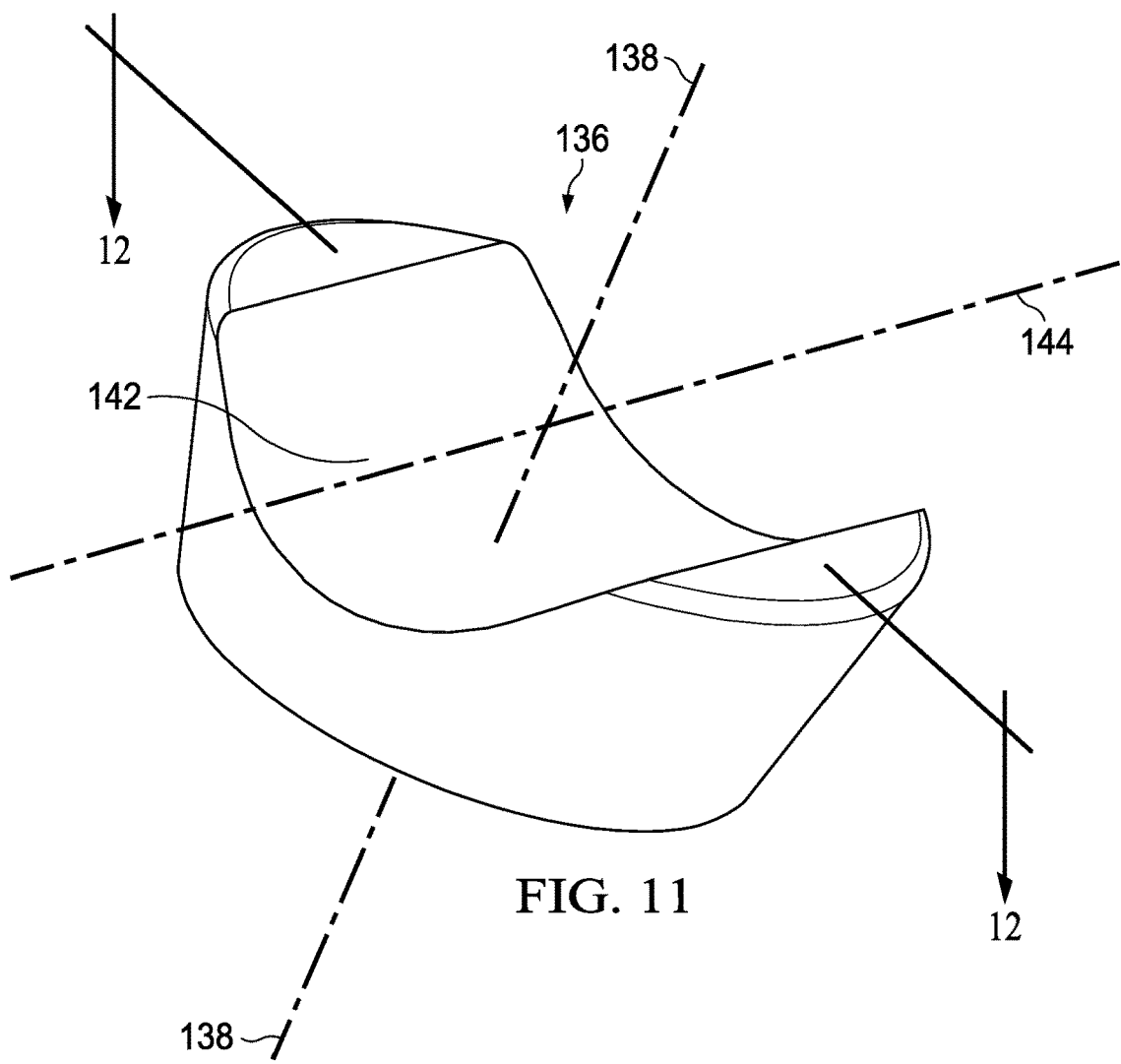
FIG. 11 is a perspective view of a spinal fixation rod cradle according to one embodiment of the disclosure.
Figure 12:
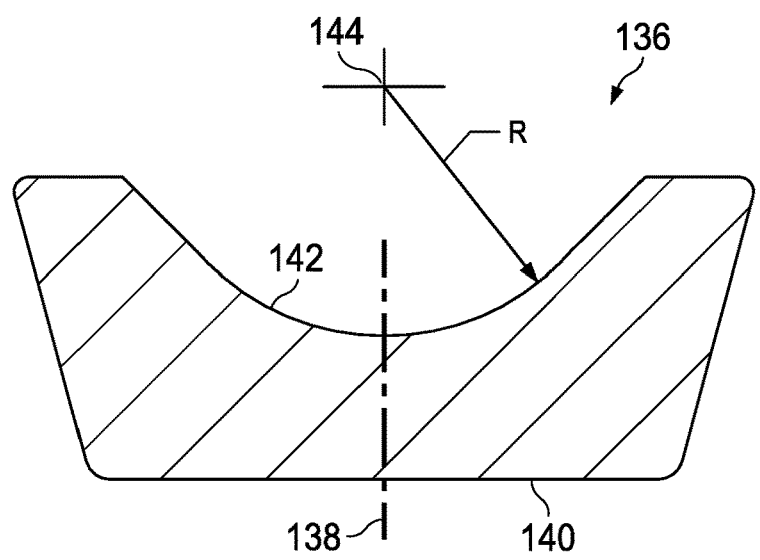
FIG. 12 depicts a cross-sectional view of section 12-12 of FIG. 11.
Figure 13:
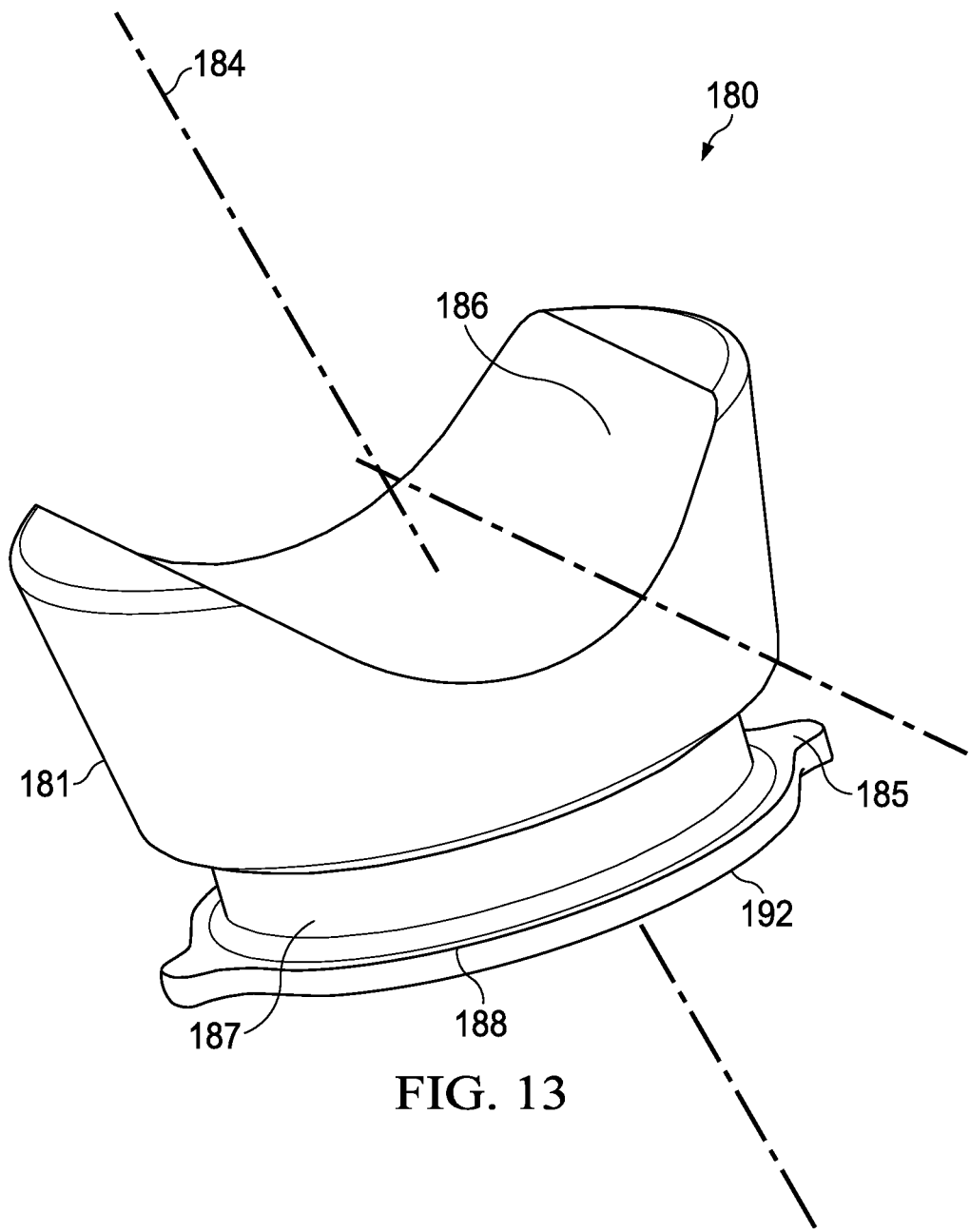
FIG. 13 is a perspective view of a spinal fixation rod cradle according to one embodiment of the disclosure.

To aid in the secure joining of non-parallel spinal rod ends, one of the spinal rod openings, for example the second spinal rod passage 122 shown in FIGS. 3-5, can have disposed therein a spinal rod cradle rest 136, shown in more detail in FIGS. 11-13. Referring to FIGS. 11 and 12, an example spinal rod cradle rest 136 can be a generally circular-shaped member having straight sidewalls (FIG. 4) or inwardly tapering sidewalls (FIGS. 11-13), the sidewalls joining a contoured upper surface 142, which can be a spinal rod-contacting surface, to a cradle base 140 which can be a relatively flat surface that rests in moveable contact with the first passage surface 182 of the second spinal rod passage 122. The spinal rod cradle rest 136 can have a central cradle axis 138 oriented perpendicular to the cradle base 140 and which, when used in a the polyaxial connector 100, can be co-axial with the second set screw axis 128. The contoured upper surface 142 can have a radius of curvature R, the radius of curvature R being from a cradle rest axis 144, and which can approximate to the radius of a spinal fixation rod, which can be about 2.25 mm to about 4.25 mm.

Thus, the spinal rod cradle rest 136 can be disposed in a spinal rod passage, such as the second spinal rod passage 122, as rotatable member with the central cradle axis 138 generally co-axial with the second set screw axis 128. As depicted in FIG. 4, the spinal rod cradle rest 136 can be fitted in a notch 190 in the vertex 135 defined where each internal sidewall 132 meets at its narrowest throat portion 534, which is the narrowest portion through which a spinal fixation rod can pass to be connected by the polyaxial connector 100. A spinal fixation rod to be fixed in the second spinal rod passage 122 can be inserted with its axis aligned with the cradle rest axis 144, and the spinal rod cradle rest 136 can then be rotated about the central cradle axis 138 to align the spinal fixation rod axis with any of the variable axes, such as second axis 124B or 124C. A second spinal fixation rod can be secured by rotating the second set screw to tighten on the internal threads of the second internally threaded set screw opening 126 which then engages and tightens on the second spinal fixation rod disposed between the second set screw and the contoured upper surface 142 of the spinal rod cradle rest 136. Thus, the second spinal fixation rod can be secured at a selected angle relative to the first spinal fixation rod, with the second spinal fixation rod being secured by the second set screw urging the second spinal fixation rod against the curved shape of the spinal rod cradle rest 136, with the cradle rest axis 144 corresponding to the direction of a selected variable rod axis.

Figure 6:
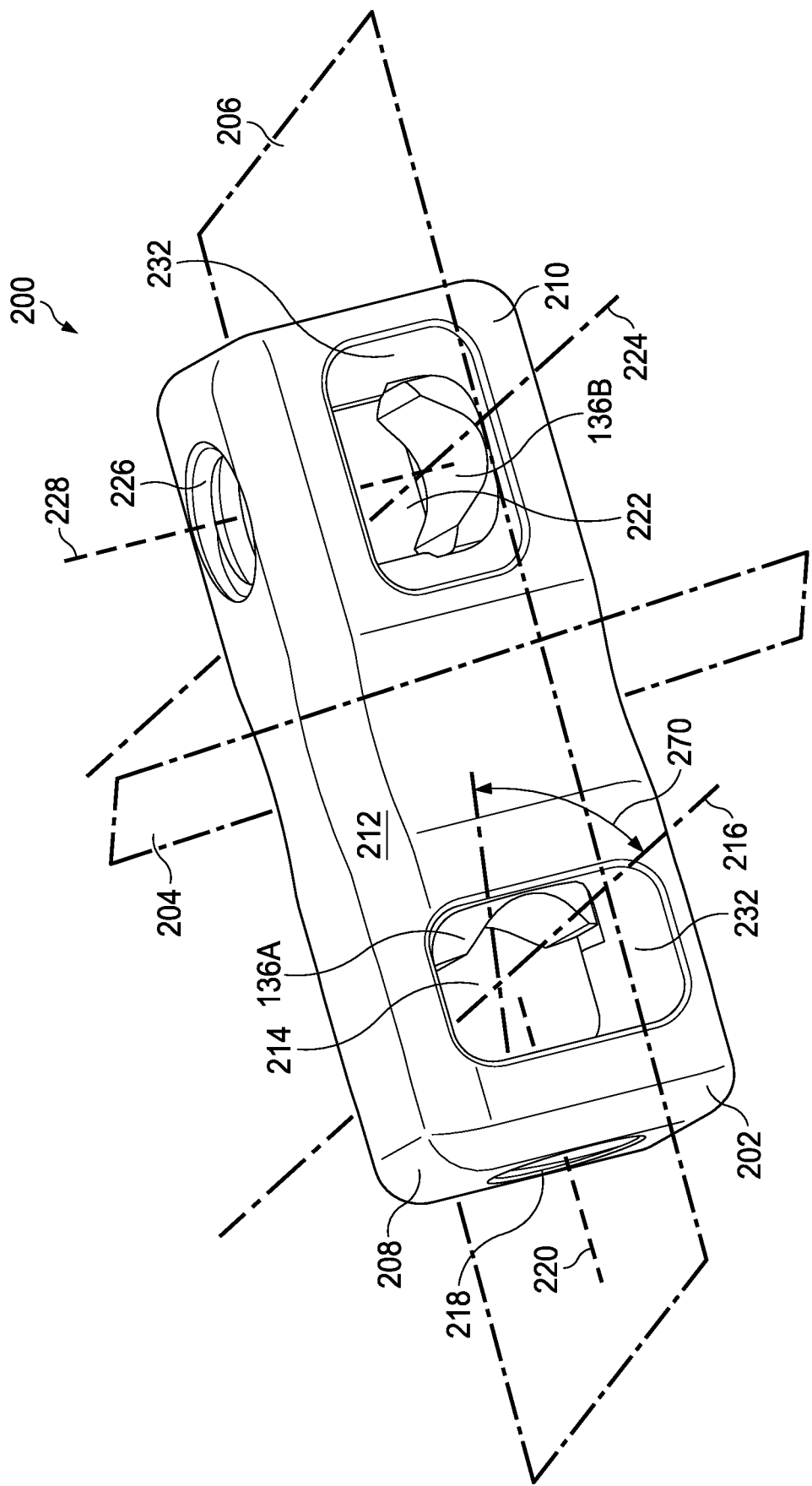
FIG. 6 is a perspective view of a representative spinal fixation rod connector according to one embodiment of the disclosure.

Referring now to FIG. 6, there is shown another embodiment of a polyaxial connector in with both of the spinal rod openings can facilitate variable axis connection of spinal fixation rods. A polyaxial connector 200 as shown can be useful for connecting the ends of two spinal fixation rods that are not parallel in the same plane. The polyaxial connector 200 has a connector body 202, which, as above, can be understood with reference to two imaginary intersecting, orthogonal planes: an imaginary first reference plane 204 and an imaginary second reference plane 206. The imaginary first reference plane 204 divides the polyaxial connector body into two portions, a first body portion 208 and a second body portion 210.

The polyaxial connector 200 has an external surface 212, the external surface defining a plurality of openings that pass through at least a portion of the polyaxial connector 200. The external surface 212 on the first body portion 208 defines openings to a first spinal rod passage 214 defining a first spinal rod passage axis 216. The first spinal rod passage 214 passes completely through the connector body 202 and serves as a passage for connecting a first spinal rod (not shown in FIG. 6, but as shown in FIGS. 1 and 2), the first spinal rod having a first spinal rod axis that can be, when connected, co-axial with the first spinal rod passage axis 216. The first spinal rod passage axis 216 can be one of a plurality of axes in virtually an infinite range of orientation that, in an embodiment, can sweep an arc 270 of, in an embodiment, up to and including 40 degrees. The external surface 212 on the first body portion 208 defines a first internally threaded set screw opening 218 defining a first set screw axis 220. A first set screw (not shown in FIG. 6, but as shown in FIGS. 1 and 2) can be screwed into the first internally threaded set screw opening 218 to engage and tighten on the first spinal rod inside the first spinal rod passage 214. Once inserted and secured, it can be understood that the end of the first spinal rod can be secured in a fixed position with reference to the imaginary first reference plane 204 and the imaginary second reference plane 206. In an embodiment, once inserted and secured, the end of the first spinal rod can be secured in a fixed position parallel to one or both of the imaginary first reference plane 204 and the imaginary second reference plane 206. In an embodiment, the first spinal rod passage axis 216 and the first set screw axis 220 are co-planar.

Referring again to FIG. 6, the external surface 212 on the second body portion 210 defines openings to a second spinal rod passage 222 defining a second spinal rod passage axis 224. As with the first spinal rod passage axis 216 and the second spinal rod passage axis 124 of FIG. 5, the second spinal rod passage axis 224 in FIG. 6 can be one of a plurality of axes in virtually an infinite range of orientation that can sweep an arc 270 of, in an embodiment, up to and including 40 degrees. The second spinal rod passage 222 passes completely through the connector body 202 and serves as a passage for connecting a second spinal rod (not shown in FIG. 3, but as shown in FIGS. 1 and 2), the second spinal rod having a second spinal rod axis that can be, when connected, co-axial with the second spinal rod passage axis 224. The external surface 212 on the second body portion 210 defines a second internally threaded set screw opening 226 defining a second set screw axis 228. The second spinal rod can be inserted in the second spinal rod passage 222. A second set screw (not shown in FIG. 3, but as shown in FIGS. 1 and 2) can be screwed into the second internally threaded set screw opening 226 to engage and tighten on the second spinal rod inside the second spinal rod passage 222. Once inserted and secured by the set screw, it can be understood that the end of the second spinal rod can be secured in a fixed position with reference to the imaginary first reference plane 204 and the imaginary second reference plane 206. In an embodiment, once inserted and secured, the end of the second spinal rod can be secured in a fixed position parallel to one or both of the imaginary first reference plane 204 and the imaginary second reference plane 206. In an embodiment, the second spinal rod passage axis 224 and the second set screw axis 228 are co-planar.

In an embodiment of a polyaxial connector, such as the polyaxial connector 200 shown in FIG. 6, both the first spinal rod passage 214 and the second spinal rod passage 222 can include therein in each a spinal rod cradle rest. Thus, first spinal rod passage 214 can have associated there with a first spinal rod cradle rest 136A, and the second spinal rod passage 222 can have a second spinal rod cradle rest 136B. The first spinal rod cradle rest 136A, and the second spinal rod cradle rest 136B can each have the structure, function and benefits as discussed above with the spinal rod cradle rest 136. In particular, the first spinal rod cradle rest 136A can have a first central cradle axis 138A oriented perpendicular to the first cradle base 140A (not shown in FIG. 6, but corresponding to the cradle base 140 described above) and which, when used in the polyaxial connector 200, can be co-axial with the first set screw axis 220. Likewise, the second spinal rod cradle rest 136B can have a second central cradle axis 138B oriented perpendicular to the second cradle base 140B (not shown in FIG. 6, but corresponding to the cradle base 140 described above) and which, when used in the polyaxial connector 200, can be co-axial with the second set screw axis 228.

As can be understood from the description herein, the polyaxial connector 200 shown in FIG. 6 permits two spinal fixation rods to be joined in a non-parallel, non-planar configuration. Both the first spinal rod passage 214 and the second spinal rod passage 222 can have hourglass-shaped cross sections, as described above. The first spinal rod passage 214 can have sides that define a generally hourglass shape across a plane parallel with the imaginary first reference plane 204. The second spinal rod passage 222 can have sides that define a generally hourglass shape across a plane parallel with the imaginary second reference plane 206. Thus, a spinal fixation rod secured in the first spinal rod passage, as described above, can be secured in a range of axis orientations, each corresponding to the first spinal rod passage axis 216 and each generally parallel to the imaginary first reference plane 204. Likewise, a spinal fixation rod secured in the second spinal rod passage, as described above, can be secured in a range of axis orientations, each corresponding to the second spinal rod passage axis 224 and each generally parallel to the imaginary second reference plane 206. In this illustrated embodiment, when spinal fixation rods are secured in the polyaxial connector 200, they can be oriented generally as depicted with respect to the spinal rods shown in FIG. 7, described in more detail below.

In can be observed in the embodiments of polyaxial connectors depicted in FIGS. 3-6 that the various features described herein can be utilized and oriented in beneficial variations with the structure, function and benefits best described with respect to the imaginary reference frames. Thus, the polyaxial connector 100 shown in FIGS. 3-5, illustrates that in certain embodiments, a first spinal rod passage can be generally cylindrical and a second spinal rod passage can have a generally hourglass shaped cross section. Also, a first set screw axis and second set screw axis can be parallel and co-planar. Additionally, a first set screw axis and a second set screw axis can be parallel to an imaginary first plane. Reference to the polyaxial connector 200 in FIG. 6, illustrates that in certain embodiments, both a first spinal rod passage and a second spinal rod passage can each have a generally hourglass shaped cross section. Also, a first set screw axis and second set screw axis can be perpendicular and co-planar. Additionally, a first set screw axis can be perpendicular to one of the imaginary first reference plane or the second reference plane, and a second set screw axis can be parallel to one of the imaginary first reference plane or the second reference plane. While not shown, it can be understood that further configurations can be achieved. For example, similar to the embodiment of a polyaxial connector 200 in FIG. 6, the second spinal rod passage 222 can have a second internally threaded set screw opening 226 defining a second set screw axis 228 that is co-axial with the first set screw axis 220.

Figure 7:
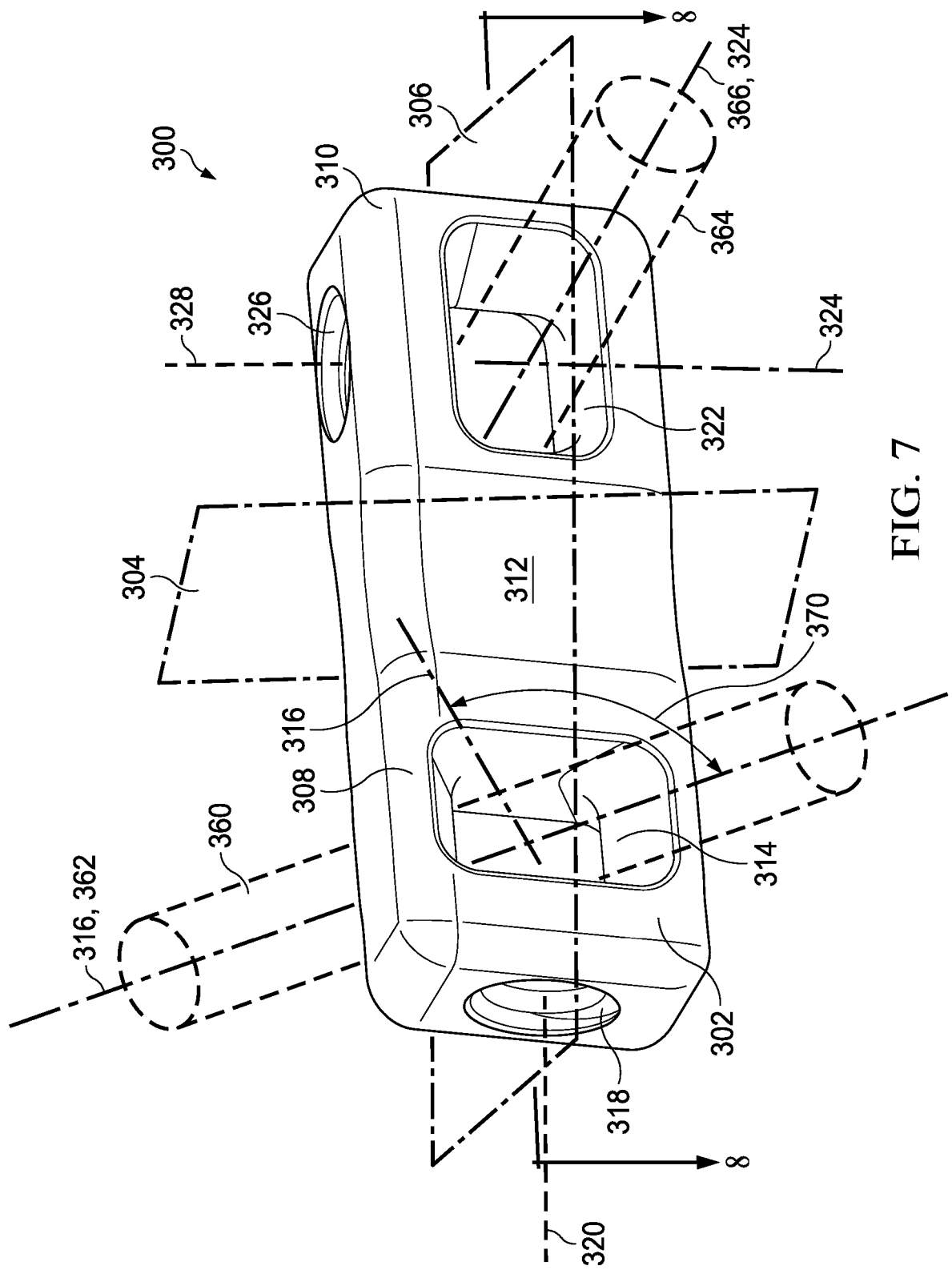
FIG. 7 is a perspective view of a representative spinal fixation rod connector according to one embodiment of the disclosure.

In general, it can be observed that a polyaxial connector can include a spinal rod cradle rest in none, one, or both, of the spinal rod passages. For example, in the example depicted in FIGS. 3-5, one of the spinal rod passages utilizes a spinal rod cradle rest. In the example embodiment depicted in FIG. 6, both of the spinal rod passages utilize a spinal rod cradle rest. Referring now to FIG. 7, there is shown a polyaxial connector in which no spinal rod cradle rests are utilized. The polyaxial connector depicted in FIG. 7 can be generally as described as the polyaxial connector 200 above, but without a spinal rod cradle rest in either of the first spinal rod passages. Referring to FIG. 7, there is shown a polyaxial connector 300 that includes a connector body 302, which, as above, can be understood with reference to two imaginary intersecting, orthogonal planes: an imaginary first reference plane 304 and an imaginary second reference plane 306. The imaginary first reference plane 304 divides the connector body 302 into two portions, a first body portion 308 and a second body portion 310.

The polyaxial connector 300 has an external surface 312, the external surface defining a plurality of openings that pass through at least a portion of the polyaxial connector 300. The external surface 312 on the first body portion 308 defines openings to a first spinal rod passage 314 defining a first spinal rod passage axis 316. As discussed above, the first spinal rod passage axis 316 can be one of a plurality of axes in virtually an infinite range of orientation that can sweep an arc 370 of, in an embodiment, up to and including 40 degrees. The first spinal rod passage 314 passes completely through the connector body 302 and serves as a passage for connecting a first spinal rod 360, the first spinal rod 360 having a first spinal rod axis 362 that can be, when connected, co-axial with the first spinal rod passage axis 316. The external surface 312 on the first body portion 308 defines a first internally threaded set screw opening 318 defining a first set screw axis 320. A first set screw (not shown in FIG. 7, but as shown in FIGS. 1 and 2) can be screwed into the first internally threaded set screw opening 318 to engage and tighten on the first spinal rod 360 inside the first spinal rod passage 314. Once inserted and secured, it can be understood that the end of the first spinal rod 360 can be secured in a fixed position with reference to the imaginary first reference plane 304 and the imaginary second reference plane 306. In an embodiment, once inserted and secured, the end of the first spinal rod 360 can be secured in a fixed position parallel to one or both of the imaginary first reference plane 304 and the imaginary second reference plane 306. In an embodiment, the first spinal rod passage axis 316 and the first set screw axis 320 are co-planar.

Referring again to FIG. 7, the external surface 312 on the second body portion 310 defines openings to a second spinal rod passage 322 defining a second spinal rod passage axis 324. The second spinal rod passage 322 passes completely through the connector body 302 and serves as a passage for connecting a second spinal rod 364, the second spinal rod 364 having a second spinal rod axis 366 that can be, when connected, co-axial with the second spinal rod passage axis 324. The external surface 312 on the second body portion 310 defines a second internally threaded set screw opening 326 defining a second set screw axis 328. The second spinal rod 364 can be inserted in the second spinal rod passage 322. A second set screw (not shown in FIG. 3, but as shown in FIGS. 1 and 2) can be screwed into the second internally threaded set screw opening 326 to engage and tighten on the second spinal rod 364 inside the second spinal rod passage 322. Once inserted and secured by the set screw, it can be understood that the end of the second spinal rod 364 can be secured in a fixed position with reference to the imaginary first reference plane 304 and the imaginary second reference plane 306. In an embodiment, once inserted and secured, the end of the second spinal rod 364 can be secured in a fixed position such that the second spinal rod axis 366 is parallel to one or both of the imaginary first reference plane 304 and the imaginary second reference plane 306. In an embodiment, the second spinal rod passage axis 324 and the second set screw axis 328 are co-planar.

Figure 8:
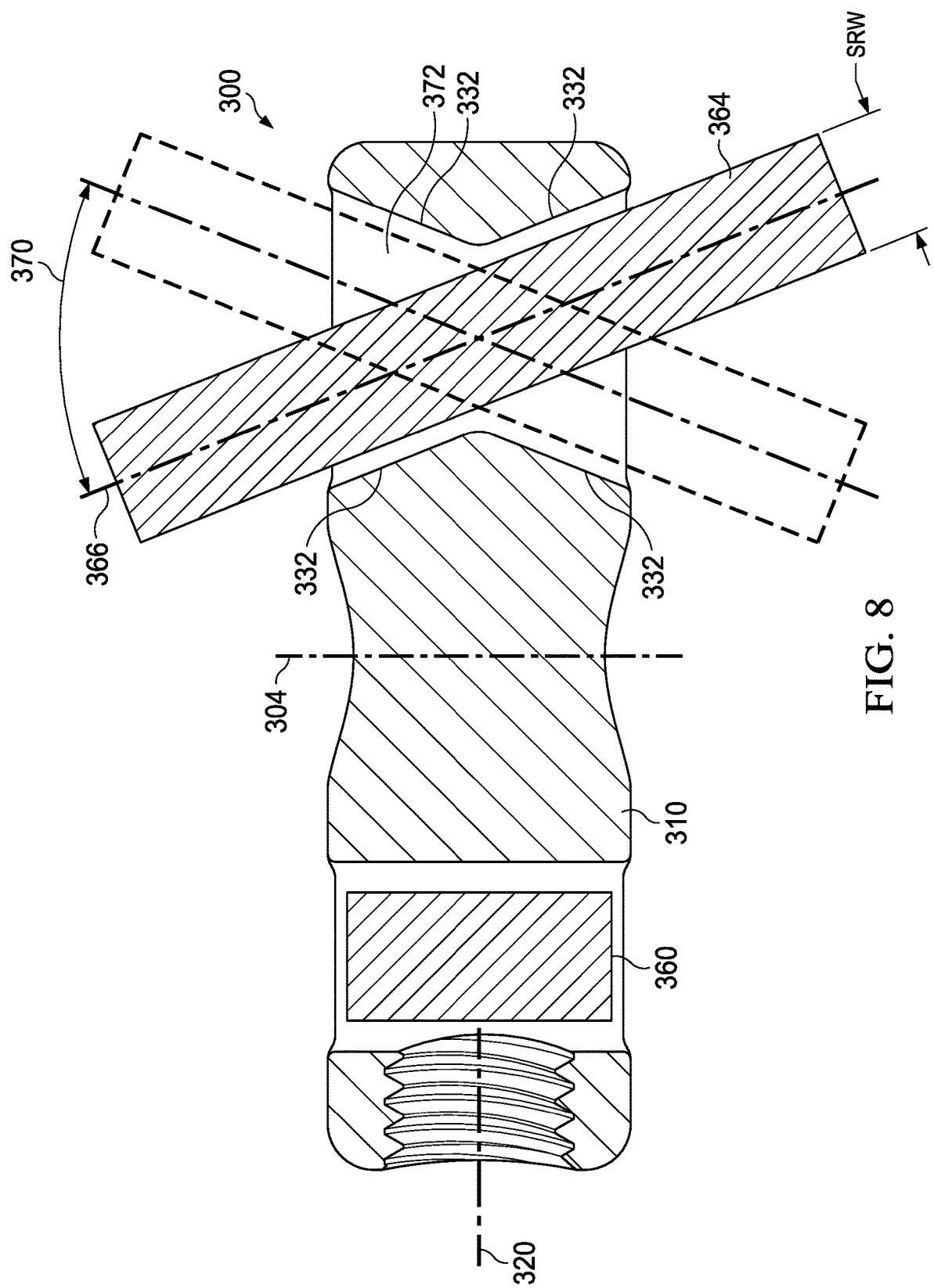
FIG. 8 is a cross-sectional view of the cross-section 8-8 of FIG. 7.

Referring now to FIG. 8, certain benefits and advantages of the hourglass shaped cross section of a spinal rod passage are illustrated. As discussed above, the generally hourglass cross sectional shape of a spinal rod passage, such as second spinal rod passage 322 in FIGS. 7 and 8, permits the securement of a spinal rod, such as the second spinal rod 364 in a range of axial orientations with respect to an imaginary reference plane, such as imaginary first reference plane 304. By way of example, second spinal rod 364 can be secured in the second spinal rod passage 322 by the second set screw threaded into the second internally threaded set screw opening 326, which can tighten on the second spinal rod as it is pressed against the opposite side, i.e., surface 372 in FIG. 8. The second spinal rod 364 can be secured in a range of axial orientations within an arc 370, which in example embodiments can be up to and include 40 degrees, and which corresponds, for example, to the range of the second spinal rod passage axis 124, shown in FIG. 3. As discussed with reference to FIG. 5, the parallel opposing internal sides 332 of the second spinal rod passage 322 can be spaced to conform at least to the width of a spinal rod SRW to provide for additional securement surfaces. Thus, a first spinal fixation rod can be secured in one spinal rod passage at an angle with respect to an imaginary reference plane, and, in certain embodiments, at an angle with respect to a second spinal fixation rod. In an embodiment, a first spinal fixation rod can be secured in a non-planar, non-parallel orientation with respect to a second spinal fixation rod.

Figure 9:
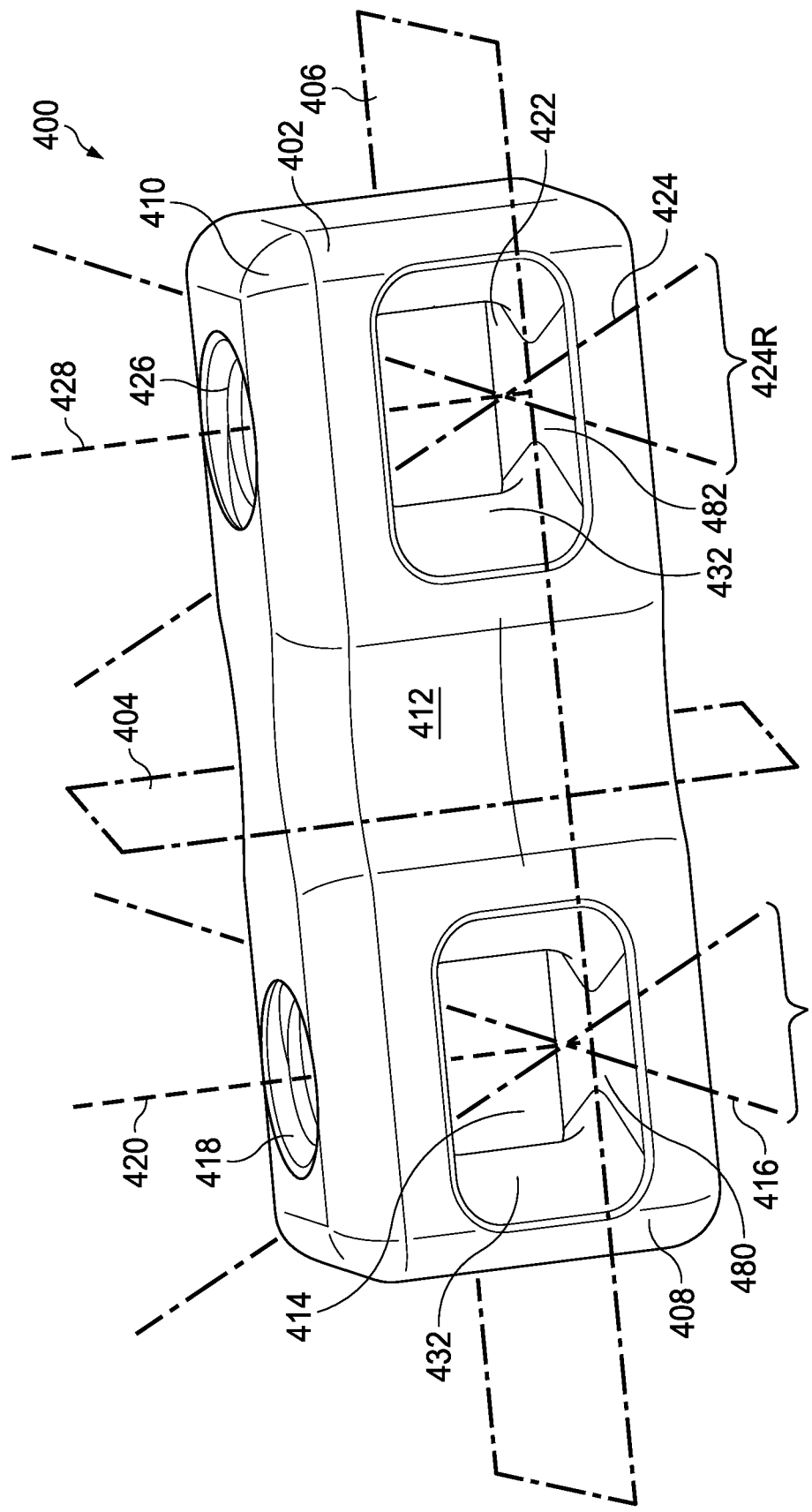
FIG. 9 is a perspective view of a representative spinal fixation rod connector according to one embodiment of the disclosure.
Figure 10:
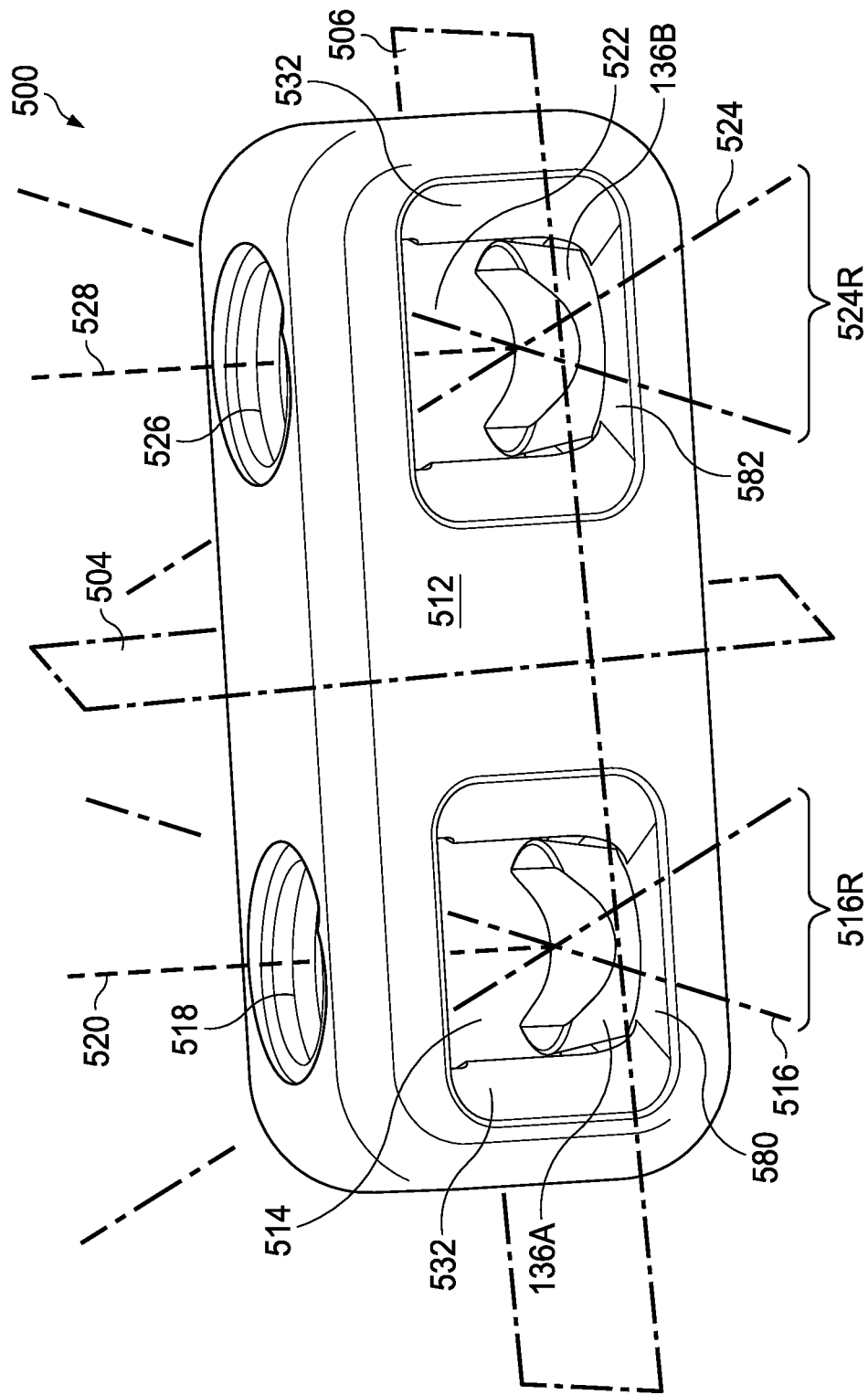
FIG. 10 is a perspective view of a representative spinal fixation rod connector according to one embodiment of the disclosure.

Referring now to FIGS. 9 and 10, there are shown embodiments of example polyaxial connectors in which two spinal fixation rods can be connected in a planar, non-parallel configuration. The example embodiments build on the structures and design principles disclosed hereinabove, and include alternative structures and features that provide for added flexibility in spinal rod fixation. Without repeating all the common features evident on and described above, the following features are described. The connector 400 of FIG. 9 exhibits a first spinal rod passage 414 having sidewalls 432 that, as described above, converge internally to define a shape that in cross section at imaginary second reference plane 406 generally approximates an hourglass shape. Thus, a spinal rod secured in the first spinal rod passage 414 can be positioned with its axis generally parallel to and/or co-axial to the first spinal rod passage axis 416, which can be one of any within the first spinal rod passage axes range 416R, each of which are substantially parallel to the imaginary second reference plane 406. The first spinal rod passage axes range 416R represents what is virtually an infinite range of axis orientation that can sweep an arc of, in an embodiment, up to and including 40 degrees. The connector 400 also exhibits a first internally threaded set screw opening 418 defining a first set screw axis 420. The first spinal rod passage 414 can have a first passage surface 480 which can be a generally flat interior surface disposed opposite the first internally threaded set screw opening 418. In use, a spinal fixation rod inserted into the first spinal rod passage 414 can be oriented parallel to a first spinal rod passage axis 416, which can be one of a range of first spinal rod passage axes 416A, the range being up to and including 40 degrees, and can be secured by a set screw threaded into the first internally threaded set screw opening 418 toward the first passage surface 480, thereby securing the spinal fixation rod between the tightened set screw and the first passage surface.

Likewise, the connector 400 exhibits a second spinal rod passage 422 having sidewalls 432 that, as described above, converge internally to define a shape that in cross section at imaginary second reference plane 406 generally approximates an hourglass shape. Thus, a spinal rod secured in the second spinal rod passage 422 can be positioned with its axis generally parallel to and/or co-axial to the second spinal rod passage axis 424, which can one of any within the second spinal rod passage axis range 424R, each of which are substantially parallel to the imaginary second reference plane 406. The second spinal rod passage axes range 424R represents what is virtually an infinite range of axis orientation that can sweep an arc of, in an embodiment, up to and including 40 degrees. The connector 400 also exhibits a second internally threaded set screw opening 426 defining a second set screw axis 428. The second spinal rod passage 422 can have a second passage surface 482 which can be a generally flat interior surface disposed opposite the second internally threaded set screw opening 426. In use, a spinal fixation rod inserted into the second spinal rod passage 422 can be oriented parallel to a second spinal rod passage axis 424, which can be one of any within the second spinal rod passage axis range 424R of up to and including 40 degrees, and can be secured by a set screw threaded into the second internally threaded set screw opening 426 toward the second passage surface 482, thereby securing the spinal fixation rod between the tightened set screw and the second passage surface.

The connector 500 of FIG. 10 exhibits similar features as described above with respect to connector 400 shown in FIG. 9, but with the difference being that both of the spinal rod passages include a first spinal rod cradle rest 136A, as described above and with reference to FIGS. 11 and 12, to provide for enhanced securement of a spinal fixation rod, as discussed above. The connector 500 can have a first spinal rod passage 514 having sidewalls 532 that, as described above, converge internally to define a shape that in cross section at imaginary second reference plane 506 generally approximates an hourglass shape. Thus, a spinal rod secured in the first spinal rod passage 514 can be positioned with its axis generally parallel to and/or co-axial to the first spinal rod passage axis 516, which can be one of any within the first spinal rod passage range 516R, each of which can be substantially parallel to the imaginary second reference plane 506. The first spinal rod passage axes range 516R represents what is virtually an infinite range of axis orientation that can sweep an arc of, in an embodiment, up to and including 40 degrees. The connector 500 also exhibits a first internally threaded set screw opening 518 defining a first set screw axis 520. The first spinal rod passage 514 can have a first passage surface 580 which can be a generally flat interior surface disposed opposite the first internally threaded set screw opening 518. The first spinal rod cradle rest 136A can be disposed in the first spinal rod passage 514 such that the cradle base 140 rests in moveable contact with the first passage surface 580 of the first spinal rod passage 514. The first spinal rod cradle rest 136A can be at least partially secured in the first spinal rod passage 514 by a notch in the sidewall vertex 535, as described above. The first spinal rod cradle rest 136A can have a central cradle axis 138 oriented perpendicular to the cradle base 140 and which, when used in a connector 500, can be co-axial with the first set screw axis 520 such that a spinal fixation rod to be fixed in the first spinal rod passage 514 can be inserted with its axis aligned with the cradle rest axis 144, and the first spinal rod cradle rest 136A can then be rotated about the central cradle axis 138 to align the spinal fixation rod axis which can be oriented parallel to a first spinal rod passage axis 516, and which can one of any within the first spinal rod passage range 516R, each of which are substantially parallel to the imaginary second reference plane 506. The spinal fixation rod can be secured by a set screw threaded into the first internally threaded set screw opening 518 toward the first passage surface 580, thereby securing the spinal fixation rod between the tightened set screw and the contoured upper surface 142 of the first spinal rod cradle rest 136A.

Likewise, the connector 500 can have a second spinal rod passage 522 having sidewalls 532 that, as described above, converge internally to define a shape that in cross section at imaginary second reference plane 506 generally approximates an hourglass shape. Thus, a spinal rod secured in the second spinal rod passage 522 can be positioned with its axis generally parallel to and/or co-axial to the second spinal rod passage axis 524, which can be one of any within the second spinal rod passage range 524R, each of which can be substantially parallel to the imaginary second reference plane 506. The second spinal rod passage axes range 424R represents what is virtually an infinite range of axis orientation that can sweep an arc of, in an embodiment, up to and including 40 degrees. The connector 500 also exhibits a second internally threaded set screw opening 526 defining a second set screw axis 528. The second spinal rod passage 522 can have a second passage surface 582 which can be a generally flat interior surface disposed opposite the second internally threaded set screw opening 526. A second spinal rod cradle rest 136B can be disposed in the second spinal rod passage 522 such that the cradle base 140 rests in moveable contact with the second passage surface 582 of the second spinal rod passage 522. The second spinal rod cradle rest 136B can be at least partially secured in the second spinal rod passage 522 by a notch in the sidewall vertex 535, as described above. The second spinal rod cradle rest 136B can have a central cradle axis 138 oriented perpendicular to the cradle base 140 and which, when used in a connector 500, can be co-axial with the second set screw axis 528 such that a spinal fixation rod to be fixed in the second spinal rod passage 522 can be inserted with its axis aligned with the cradle rest axis 144, and the second spinal rod cradle rest 136B can then be rotated about the central cradle axis 138 to align the spinal fixation rod axis which can be oriented parallel to a second spinal rod passage axis 524, and which can one of any within the second spinal rod passage range 524R, each of which are substantially parallel to the imaginary second reference plane 506. The spinal fixation rod can be secured by a set screw threaded into the second internally threaded set screw opening 526 toward the second passage surface 582, thereby securing the spinal fixation rod between the tightened set screw and the contoured upper surface 142 of the second spinal rod cradle rest 136B.

FIGS. 11 and 12 depict a spinal rod cradle rest 136, which can be used to enhance the securement of a spinal fixation rod in a polyaxial connector, as discussed above.

FIG. 13 depicts another example of a spinal rod cradle rest. The spinal rod cradle rest 180 can be a generally circular-shaped member having a cradle base 192 which can be a relatively flat surface that rests in moveable contact with the first passage surface of a spinal rod passage, as discussed above. The spinal rod cradle rest 180 can have a central cradle axis 184 oriented perpendicular to the cradle base 192 and which, when used in a polyaxial connector can be co-axial with the set screw axis. The spinal rod cradle rest 180 can have a contoured upper surface 186 having a having a radius of curvature as discussed above with respect to the spinal rod cradle rest 136. The spinal rod cradle rest 180 can have an engagement member, which can be a groove 187 and/or a circumferentially extending rib 188, either or both of which can be disposed in a cooperating relationship with similar features on the connector in the spinal rod passage in which they are disposed. Groove 187 can be a portion of the spinal rod cradle rest 180 that is indented relative to an outer side wall of the spinal rod cradle rest 180, such as side wall 181. The circumferentially extending rib 188 can be a member that extends outwardly from portions of the spinal rod cradle rest 180, and which can also include further extensions, such as one or more tabs 185. As can be understood, the groove 187 and/or a circumferentially extending rib 188 feature(s) can be utilized to cooperate with mating features on a polyaxial connector to aid in securing the spinal rod cradle axis in the connector prior to use in securing a spinal fixation rod in the connector.

Referring to the above-described examples, the connectors can be characterized as having two spinal rod passages in which the respective set screw axes are parallel and planar (e.g., FIGS. 3-5 and 9-10) or perpendicular and planar (e.g., FIGS. 6-8). Further, they can be characterized as including a spinal rod cradle rest in one spinal rod passage (e.g., FIGS. 3-5) or two spinal rod passages (e.g., FIGS. 6 and 10), or neither spinal rod passage (e.g., FIG. 7-9).

Referring to FIGS. 14-22, there are shown example embodiments of polyaxial connectors that include and build on the structures and design principles disclosed hereinabove, and which include alternative structures and features that provide for added flexibility in spinal rod fixation. That is, the example connectors depicted and described in FIGS. 14-22 can include any and all of the features described above, but which features, in the interest of conciseness, are not fully described again. Thus, for example, the polyaxial connector 600 described below is not shown utilizing a spinal rod cradle rest in either spinal rod passage, yet it is understood that the polyaxial connector 600 can optionally include a spinal rod cradle rest in either or both spinal rod passages, based on the descriptions herein.

Figure 14:
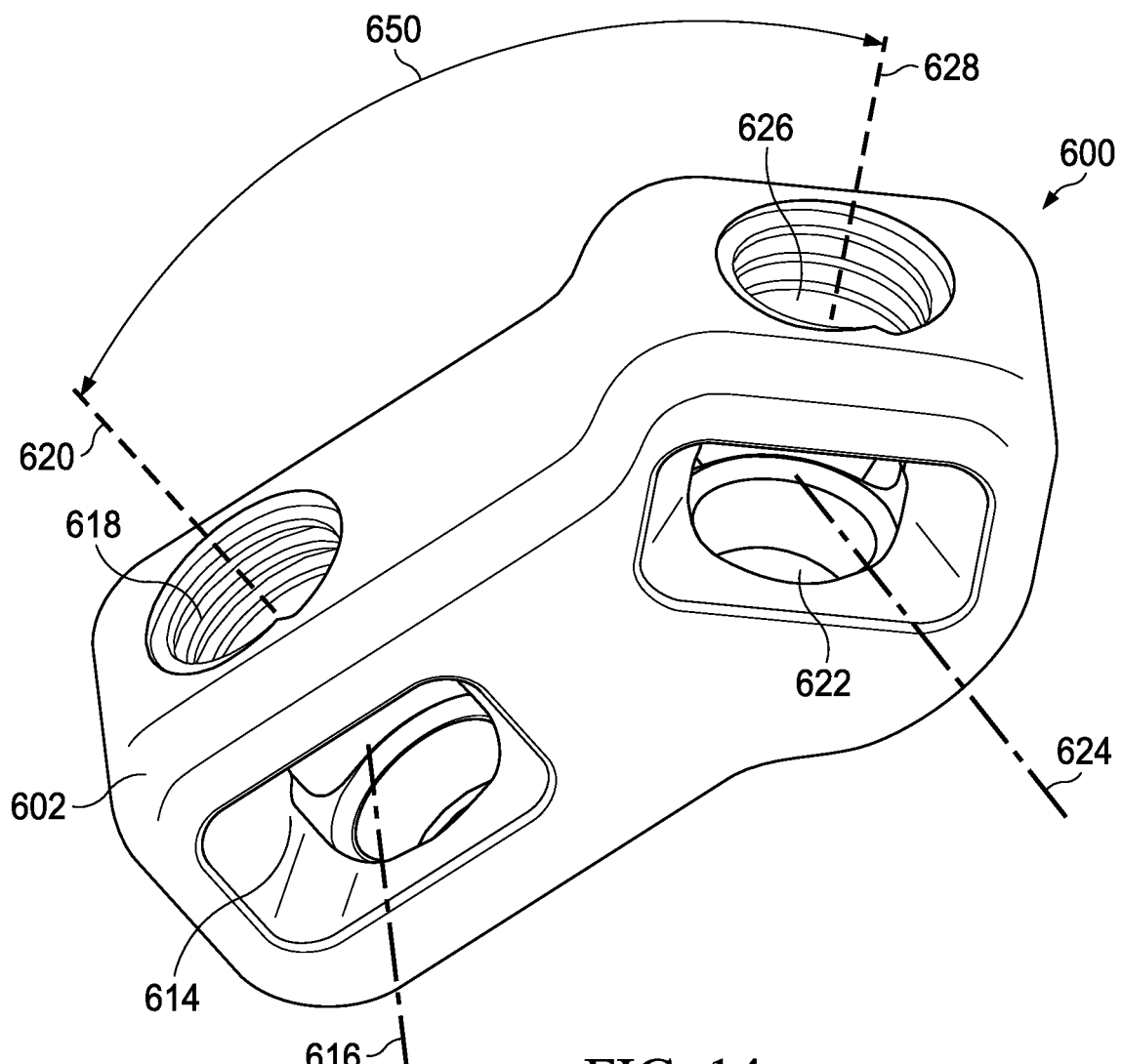
FIG. 14 is a perspective view of a representative spinal fixation rod connector according to one embodiment of the disclosure.

Polyaxial connector 600 shown in FIG. 14 has connector body 602 including a first spinal rod passage 614 defining a first spinal rod passage axis 616 and a first internally threaded set screw opening 618 defining a first set screw axis 620. The polyaxial connector 600 can have a second spinal rod passage 622 defining a second spinal rod passage axis 624 and a second internally threaded set screw opening 626 defining a second set screw axis 628. The polyaxial connector 600 can be described as a hybrid of the previously described connectors, in that the respective set screw axes are non-perpendicular, non-parallel and planar. The respective set screw axes can sweep an angle 650 of between 1 degree and 89 degrees to provide enhanced flexibility with respect to the mutual orientation of connected spinal fixation rods.

Figure 15:
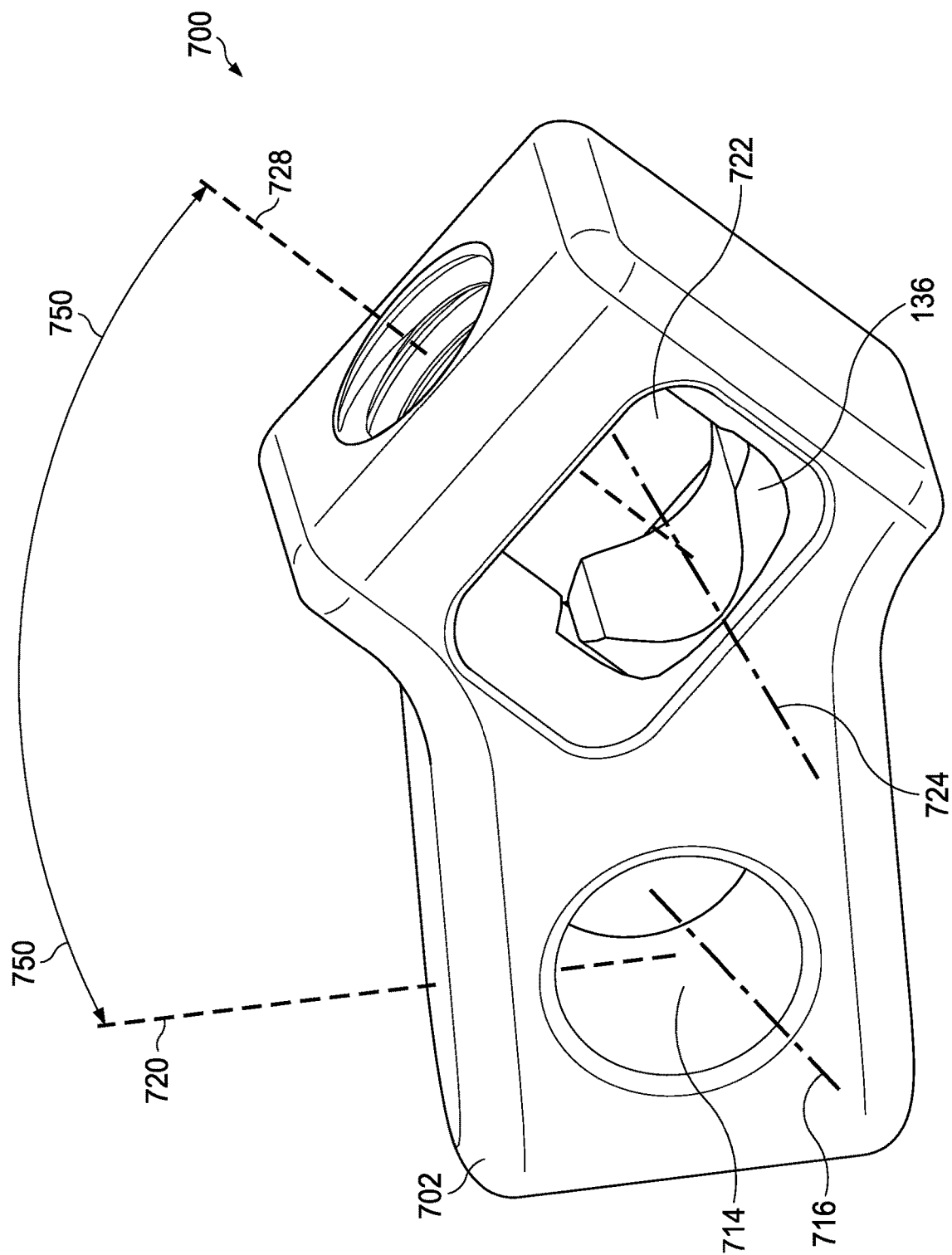
FIG. 15 is a perspective view of a representative spinal fixation rod connector according to one embodiment of the disclosure.

Polyaxial connector 700 shown in FIG. 15 has connector body 702 including a first spinal rod passage 714 defining a first spinal rod passage axis 716. The polyaxial connector 700 can have a second spinal rod passage 722 defining a second spinal rod passage axis 724 and a second internally threaded set screw opening 726 defining a second set screw axis 728. The polyaxial connector 700 can be described as a hybrid of the previously described connectors, in that the connector body 702 includes a first spinal rod passage 714 that can be a cylindrical passage, a spinal rod cradle rest 136 in one of the spinal rod passages, namely the second spinal rod passage 722, and the respective set screw axes are non-perpendicular, non-parallel and planar. The respective set screw axes can sweep an angle 750 of between 1 degree and 89 degrees to provide enhanced flexibility with respect to the mutual orientation of connected spinal fixation rods.

Figure 16:
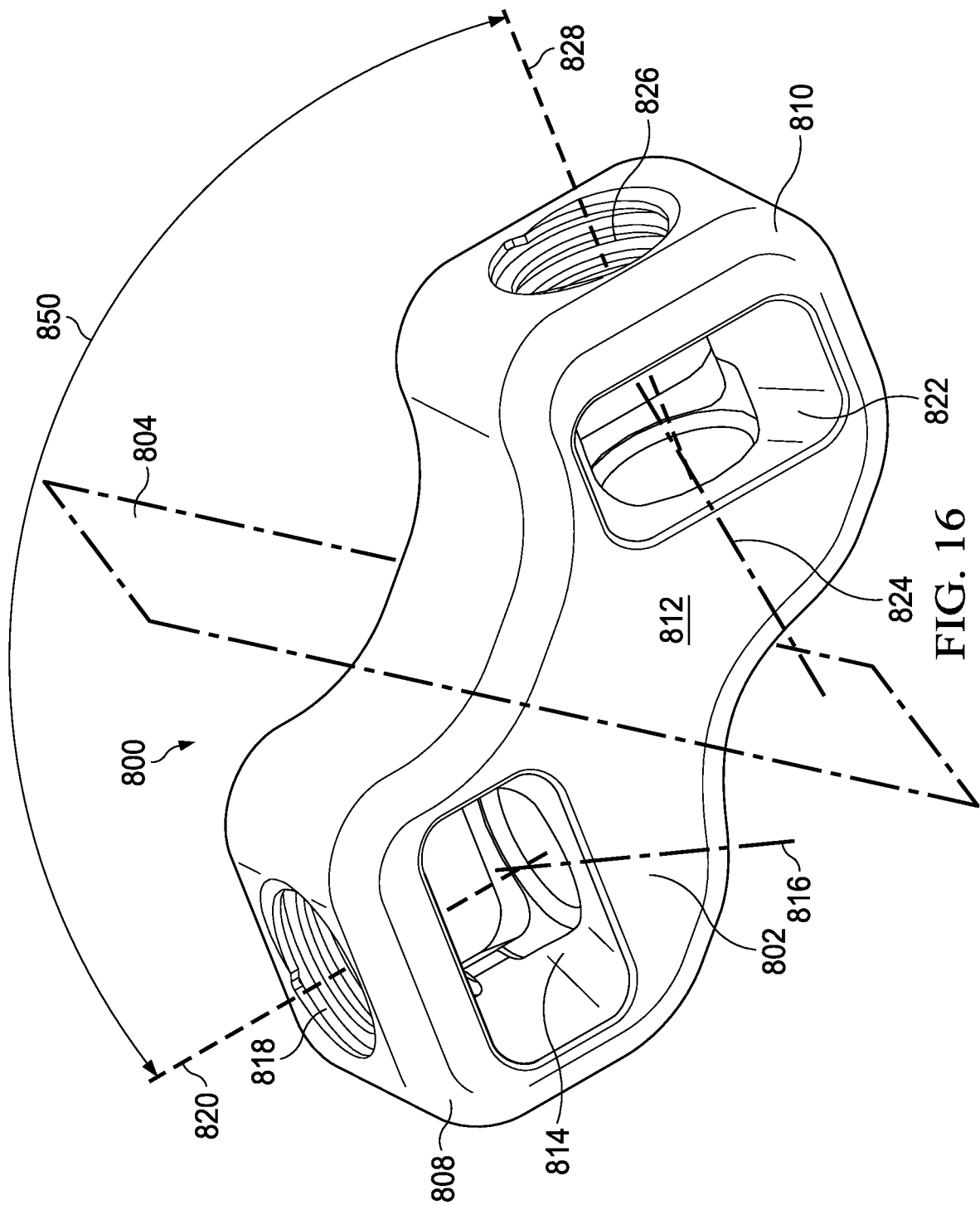
FIG. 16 is a perspective view of a representative spinal fixation rod connector according to one embodiment of the disclosure.

Polyaxial connector 800 shown in FIG. 16 has connector body 802 that can be intersected by a first imaginary reference plane 804 into a first body portion 808 and a second body portion 810, which can be substantially mirror images of one another. The first body portion 808 includes a first spinal rod passage 814 defining a first spinal rod passage axis 816 and a first internally threaded set screw opening 818 defining a first set screw axis 820. The first spinal rod passage axis 816 can be one of a plurality of axes in virtually an infinite range of orientation that, in an embodiment, can sweep an arc 270 of, in an embodiment, up to and including 40 degrees. The second body portion 810 can have a second spinal rod passage 822 defining a second spinal rod passage axis 824 and a second internally threaded set screw opening 826 defining a second set screw axis 828. The second spinal rod passage axis 824 can be one of a plurality of axes in virtually an infinite range of orientation that, in an embodiment, can sweep an arc 270 of, in an embodiment, up to and including 40 degrees. The respective set screw axes are non-perpendicular, non-parallel and planar. The respective set screw axes can sweep an angle 850 of between 0 degrees and 180 degrees, or between 1 degree and 179 degrees, to provide enhanced flexibility with respect to the mutual orientation of connected spinal fixation rods.

Figure 17:
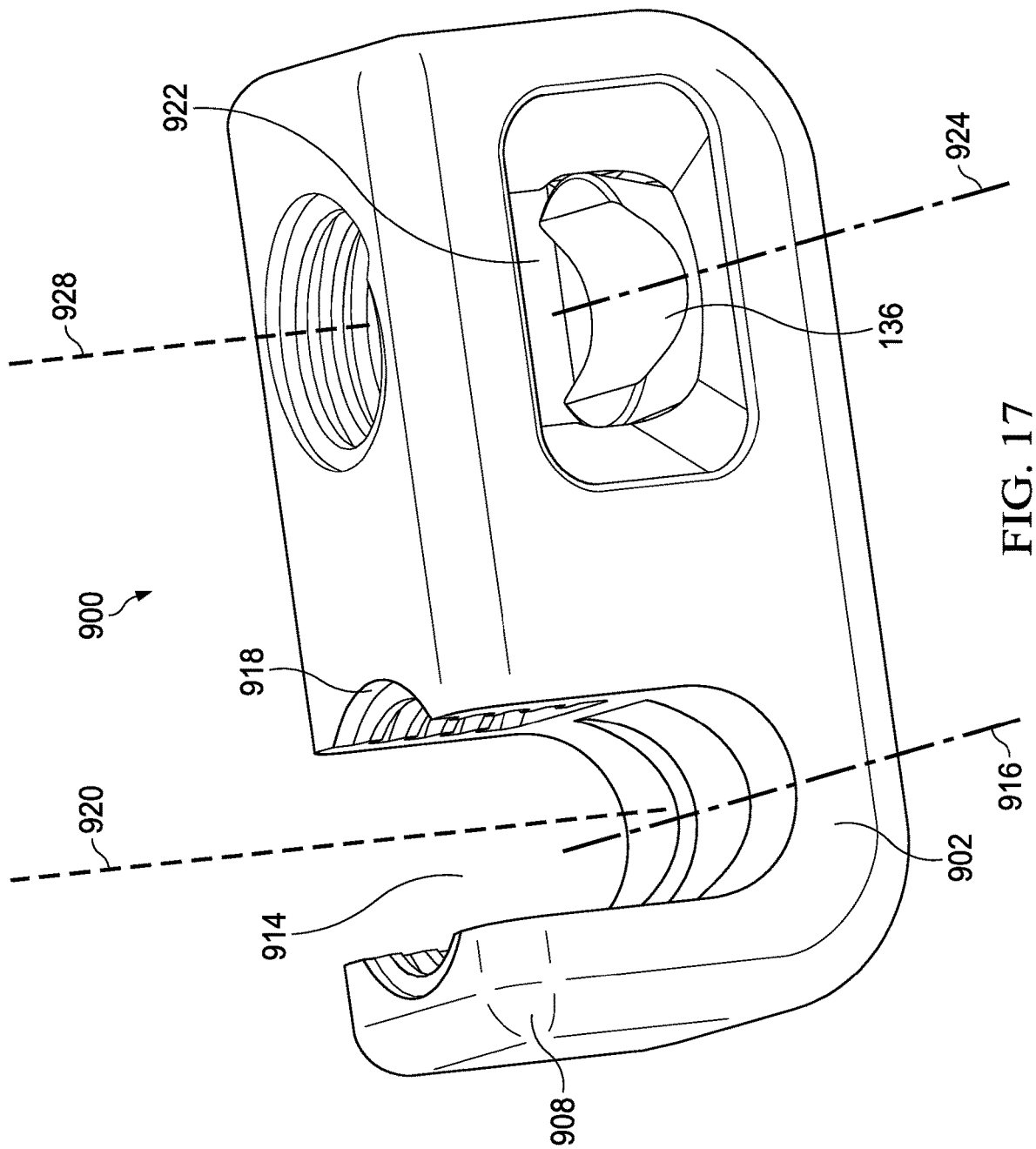
FIG. 17 is a perspective view of a representative spinal fixation rod connector according to one embodiment of the disclosure.
Figure 18:
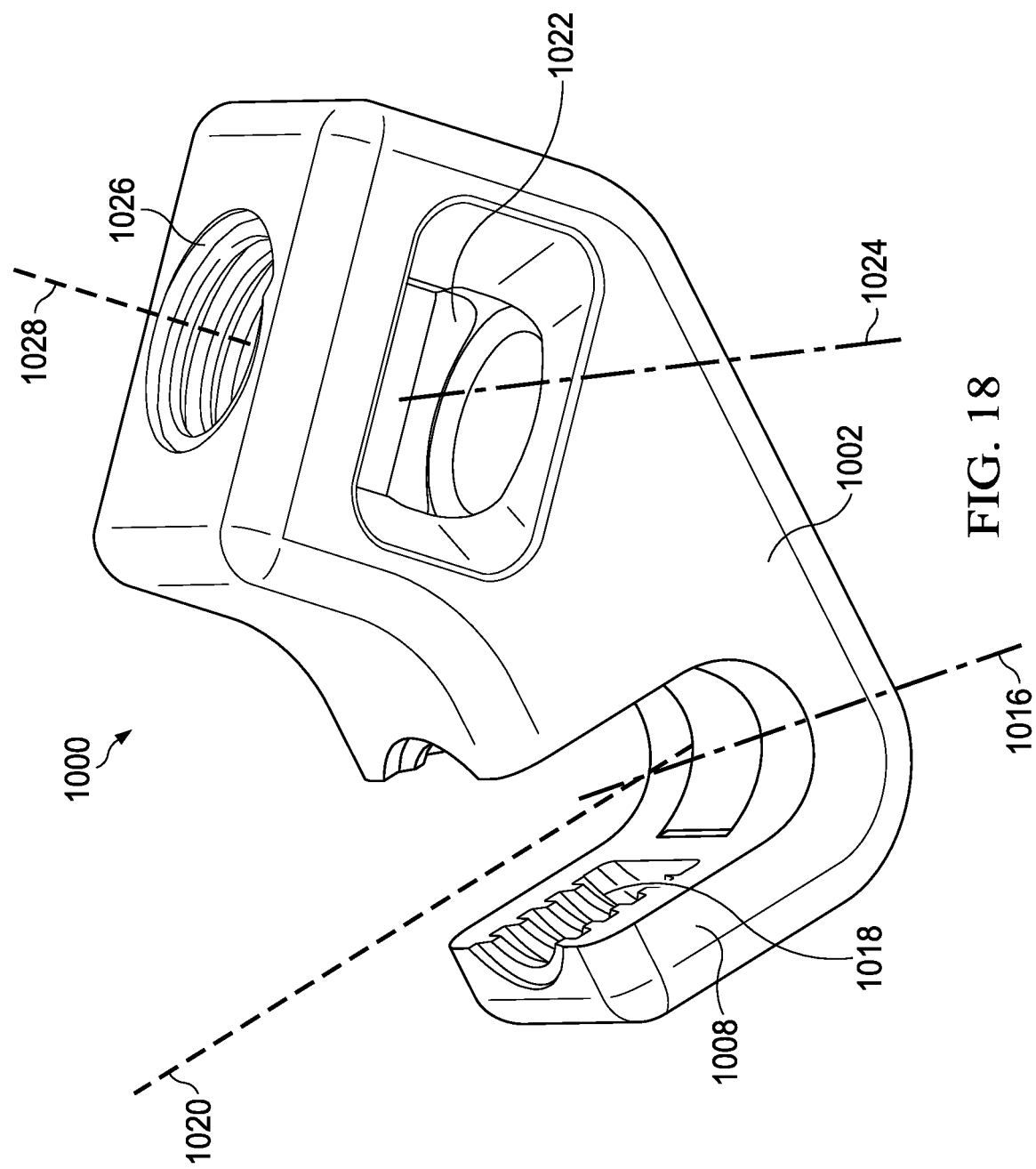
FIG. 18 is a perspective view of a representative spinal fixation rod connector according to one embodiment of the disclosure.

Referring to FIGS. 17 and 18, there are shown example embodiments of polyaxial connectors that include and build on the structures and design principles disclosed hereinabove, and which include alternative structures and features that provide for added flexibility in spinal rod fixation. That is, the example connectors depicted and described in FIGS. 17 and 18 can include any or all of the features described above, but which features, in the interest of conciseness, are not fully described again. The polyaxial connector 900 shown in FIG. 17 has a connector body 902 and a first body portion 908 including a first spinal rod passage 914 defining a first spinal rod passage axis 916. The polyaxial connector 900 can have a second spinal rod passage 922 defining a second spinal rod passage axis 924 and a second internally threaded set screw opening 926 defining a second set screw axis 928. The second spinal rod passage 922 can have a spinal rod cradle rest 136 incorporated therein. As can be understood, the polyaxial connector 900 is similar in most respects to the polyaxial connector 100 described with respect to FIG. 3. However, rather than being a cylindrical passage through the connector, the first spinal rod passage 914 of the polyaxial connector 900 can be substantially U-shaped and open at the first internally threaded set screw opening 918. With this design feature a spinal fixation rod can be introduced into the first spinal rod passage 914 from the top, through the open portion of the first internally threaded set screw opening 918, rather than being inserted, i.e., threaded, through a cylindrical shaped opening.

The connector 1000 shown in FIG. 18 has a connector body 1002 and a first body portion 1008 including a first spinal rod passage 1014 defining a first spinal rod passage axis 1016. The connector 1000 can have a second spinal rod passage 1022 defining a second spinal rod passage axis 1024 and a second internally threaded set screw opening 1026 defining a second set screw axis 1028. As can be understood, the connector 1000 is similar in most respects to the polyaxial connector 700 described with respect to FIG. 15. However, rather than being a cylindrical passage through the connector, the first spinal rod passage 1014 of the connector 1000 can be substantially U-shaped and open at the first internally threaded set screw opening 1018. With this design feature a spinal fixation rod can be introduced into the first spinal rod passage 1014 from the top, through the open portion of the first internally threaded set screw opening 1018, rather than being inserted, i.e., threaded, through a cylindrical shaped opening.

The various features of either the first portions or second portions of the connector bodies described above can also be incorporated on cylindrical extension to provide the benefits of a polyaxial connector to a lateral connector, which can be an elevated inline lateral connector, an elevated lateral connector, and the like. The connector 1100 shown in FIG. 19 can have a polyaxial connector portion 1150 that can include any of the above-described connector structures and features. Such structures and features, as described above, permit a spinal fixation rod 1152 to be secured by a set screw through a set screw threaded opening 1156 such that the spinal fixation rod central axis 1154 can be oriented at a range of orientations from a first orientation 1054A to a second orientation 1054B, through an arc of axis variation 1158. The arc of axis variation 1158 can be up to and include about 40 degrees or more.

Figure 19:
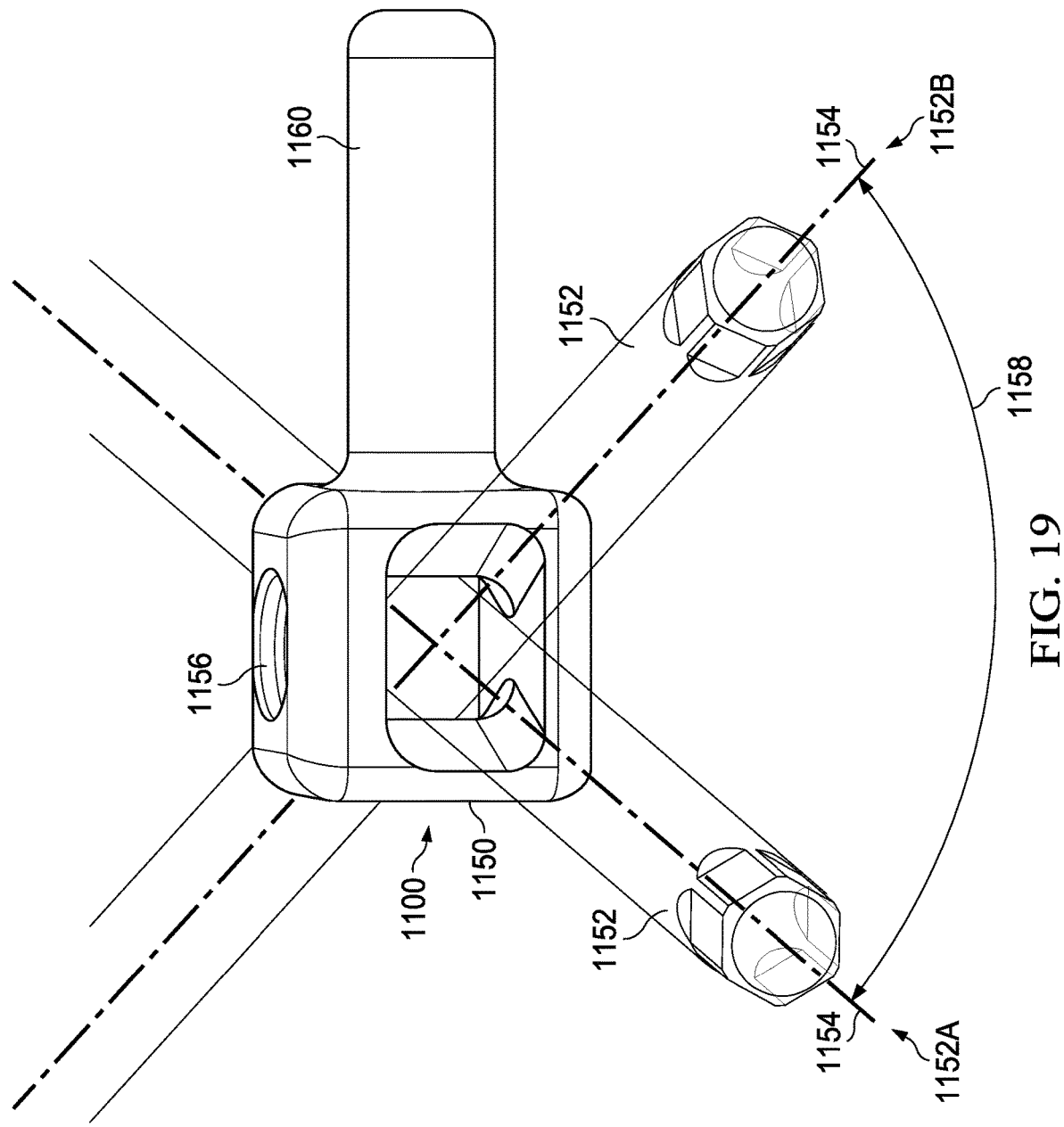
FIG. 19 is a perspective view of a representative spinal fixation rod connector with a lateral connector according to one embodiment of the disclosure.

The polyaxial connector portion 1150 can have extended from a portion thereof a lateral extension 1160, which can be a rod-like extension. The lateral extension can be substantially straight, as shown in FIG. 19, or it can be curved, including L-shaped. The lateral extension 1160 permits the polyaxial connector portion 1150 to be connected to another spinal rod fixation component, such as the tulip head of a pedicle screw, as is known in the art.

The polyaxial connectors described herein can be unitary or composed of multiple parts that are joined to make the connector. Thus, the polyaxial connectors of the present disclosure can be a unitary construction, that is, the polyaxial connector (less set screws, which are not shown), can be made of one piece construction. The polyaxial connector can be, for example, molded of a polymer material. The connector can also be, for example, formed, machined, or otherwise shaped from metal, plastic, ceramic, or other suitable materials.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

We claim:

1. A polyaxial rod connector, the polyaxial rod connector comprising a connector body, the connector body having an external surface, the connector body being intersected by an imaginary first reference plane and an imaginary second reference plane perpendicular to the imaginary first reference plane,
   a. a first body portion being on a first side of the imaginary first reference plane, the first body portion defining openings to a first spinal rod passage defining a first spinal rod passage axis and a first internally threaded set screw opening defining a first set screw axis, the first internally threaded set screw opening positioned on the first body portion to intersect the first spinal rod passage;
   b. a second body portion adjoined to the first body portion on a second side of the imaginary first reference plane, the second body portion defining openings to a second spinal rod passage defining a plurality of second spinal rod passage axes, and a second internally threaded set screw opening defining a second set screw axis, the second internally threaded set screw opening positioned on the second body portion to intersect the second spinal rod passage;
   c. wherein the first spinal rod passage axis is non-parallel with at least one of the plurality of second spinal rod passage axes in the imaginary second reference plane; and
   d. wherein one of the first spinal rod passage and the second spinal rod passage comprises a generally hourglass shaped cross section parallel to the imaginary second reference plane.

2. The polyaxial rod connector of claim 1, wherein the first spinal rod passage axis and the plurality of second spinal rod passage axes are co-planar.

3. The polyaxial rod connector of claim 1, wherein the first set screw axis and the second set screw axis are parallel and co-planar.

4. The polyaxial rod connector of claim 1, the plurality of second spinal rod passage axes sweeps an angle of between about 1 degree and about 40 degrees.

5. The polyaxial rod connector of claim 1, comprising a spinal rod cradle rest having a cradle base being disposed in movable contact with an internal surface of the second spinal rod passage, the spinal rod cradle rest comprising a central cradle axis oriented perpendicular to the cradle base and co-axial with the second set screw axis.

6. The polyaxial rod connector of claim 1, wherein the connector body is unitary and bisected by the imaginary first reference plane.

7. The polyaxial rod connector of claim 1, wherein the connector body is unitary and bisected by the imaginary second reference plane.

8. A polyaxial rod connector, the polyaxial rod connector comprising a connector body, the connector body having an external surface, the connector body being intersected by an imaginary first reference plane and an imaginary second reference plane perpendicular to the imaginary first reference plane,
   a. a first body portion being on a first side of the imaginary first reference plane, the first body portion defining openings to a first spinal rod passage defining a plurality of first spinal rod passage axes and a first internally threaded set screw opening defining a first set screw axis perpendicular to each of the plurality of first spinal rod passage axes, the first internally threaded set screw opening configured to intersect the first spinal rod passage;

b. a second body portion adjoined to the first body portion on a second side of the imaginary first reference plane, the second body portion defining openings to a second spinal rod passage defining a plurality of second spinal rod passage axes, and a second internally threaded set screw opening defining a second set screw axis perpendicular to each of the plurality of second spinal rod passage axes, the second internally threaded set screw opening configured to intersect the second spinal rod passage;

c. wherein one of the plurality of second spinal rod passage axes is non-parallel to the imaginary first reference plane; and d. wherein the second spinal rod passage comprises a generally hourglass shaped cross section parallel to the imaginary second reference plane.

9. The polyaxial rod connector of claim 8, further comprising the first spinal rod passage comprises a generally hourglass shaped cross section parallel to the imaginary first reference plane.

10. The polyaxial rod connector of claim 8, wherein the first set screw axis is perpendicular to the second set screw axis.

11. The polyaxial rod connector of claim 8, further comprising the first spinal rod passage comprises a generally hourglass shaped cross section parallel to the imaginary second reference plane.

12. The polyaxial rod connector of claim 8, wherein the first set screw axis is parallel to the second set screw axis.

13. The polyaxial spinal rod connector of claim 8, wherein the plurality of first spinal rod passage axes is parallel to the imaginary first reference plane.

14. The polyaxial rod connector of claim 8, wherein the plurality of second spinal rod passage axes are is parallel to the imaginary second reference plane.

15. The polyaxial rod connector of claim 8, comprising a first spinal rod cradle rest having a cradle base being disposed in movable contact with an internal surface of the first spinal rod passage, the first spinal rod cradle rest comprising a central cradle axis oriented perpendicular to the cradle base and co-axial with the first set screw axis.

16. The polyaxial rod connector of claim 15, further comprising a second spinal rod cradle rest having a cradle base being disposed in movable contact with an internal surface of the second spinal rod passage, the second spinal rod cradle rest comprising a central cradle axis oriented perpendicular to the cradle base and co-axial with the second set screw axis.

17. A polyaxial rod connector, the polyaxial rod connector comprising a connector body, the connector body having an external surface, the connector body being intersected by an imaginary first reference plane, a. a first body portion being on a first side of the imaginary first reference plane, the first body portion defining openings to a first spinal rod passage defining a plurality of first spinal rod passage axes and a first internally threaded set screw opening defining a first set screw axis and intersecting the first spinal rod passage;

b. a second body portion adjoined to the first body portion on a second side of the imaginary first reference plane, the second body portion defining openings to a second spinal rod passage defining a plurality of second spinal rod passage axes, and a second internally threaded set screw opening defining a second set screw axis and intersecting the second spinal rod passage;

c. wherein one of the plurality of second spinal rod passage axes is non-parallel to the imaginary first reference plane; and d. wherein the second spinal rod passage comprises a generally hourglass shaped cross section perpendicular to the second set screw axis.

18. The polyaxial rod connector of claim 17, wherein the first set screw axis and the second set screw axis are co-planar and non-parallel, sweeping an angle of between 1 degree and 179 degrees.

19. The polyaxial rod connector of claim 17, wherein neither of the plurality of first spinal rod passage axes and the plurality of second spinal rod passage axes is co-planar with the imaginary first reference plane.

20. The polyaxial rod connector of claim 17, wherein the connector body is unitary and bisected by the imaginary first reference plane.

* * * * *